US011234854B2

(12) United States Patent
Kosiorek et al.

(10) Patent No.: US 11,234,854 B2
(45) Date of Patent: Feb. 1, 2022

(54) RIGID IMMOBILIZATION SYSTEM FOR EXTREMITIES SPLINT APPARATUS, SYSTEMS AND METHODS

(71) Applicants:Christopher B. Kosiorek, La Vernia, TX (US); Esra Abir, New York, NY (US); Brenda Mee, West Newfield, ME (US); Ryan Williams, Olathe, KS (US)

(72) Inventors: Christopher B. Kosiorek, La Vernia, TX (US); Esra Abir, New York, NY (US); Brenda Mee, West Newfield, ME (US); Ryan Williams, Olathe, KS (US)

(73) Assignee: ALPHAPOINTE, Kansas City, MO (US)

( * ) Notice: Subject to any disclaimer, the term of this patent is extended or adjusted under 35 U.S.C. 154(b) by 244 days.

(21) Appl. No.: 16/258,225

(22) Filed: Jan. 25, 2019

(65) Prior Publication Data

US 2019/0224033 A1 Jul. 25, 2019

Related U.S. Application Data

(60) Provisional application No. 62/621,949, filed on Jan. 25, 2018.

(51) Int. Cl.
*A61F 5/058* (2006.01)

(52) U.S. Cl.
CPC .......... *A61F 5/05825* (2013.01); *A61F 5/058* (2013.01); *A61F 5/0585* (2013.01); *A61F 5/05858* (2013.01)

(58) Field of Classification Search
CPC .................. A61F 5/0125; A61F 5/0127; A61F 2005/0165; A61F 2005/0155;

(Continued)

(56) References Cited

U.S. PATENT DOCUMENTS 4,209,011 A 6/1980 Peck et al.
4,383,526 A 5/1983 Robins
(Continued)

FOREIGN PATENT DOCUMENTS

FR 2718346 A1 10/1995
KR 20-0271677 Y1 4/2002
(Continued)

OTHER PUBLICATIONS

International Search Report and Written Opinion received for PCT Application No. PCT/US2019/015259 dated Apr. 17, 2019.

(Continued)

*Primary Examiner* — Ophelia A Hawthorne
(74) *Attorney, Agent, or Firm* — Kutak Rock LLP; Brian L. Main

(57) ABSTRACT

A foldable splint and method of use is provided. The foldable splint includes a main body divided into a plurality of panels and segments by a grid of living hinges. Each panel includes opposed first and second outer segments and a plurality of inner segments extending therebetween. By folding the main body along segment hinges, the splint is moved to a first rigid configuration for securing an appendage in a straight configuration. By further folding the splint at opposed pinch locations, the splint is moved to a second rigid configuration for securing an appendage in a bent configuration. By folding the splint along panel hinges, the splint is moved to a third rigid configuration for securing around an abdomen or pelvis of a user. When not in use, the splint can be moved back to the stowable configuration by folding the various panels over each other.

19 Claims, 39 Drawing Sheets

(58) Field of Classification Search
CPC ...... A61F 2005/0132; A61F 2005/0144; A61F 2005/0148; A61F 5/01; A61F 2005/0134; A61F 2005/0197; A61F 2220/0091; A61F 2/604; A61F 2/64; A61F 5/05858; A61F 5/3723; A61F 5/058; A61F 5/0585; A61F 5/05825; A61G 1/01; A61G 1/044; A61G 1/00

See application file for complete search history.

(56) References Cited

U.S. PATENT DOCUMENTS

| | | | |
|---|---|---|---|
| D286,073 S | 10/1986 | Russell | |
| 4,776,327 A | 10/1988 | Russell | |
| 4,945,925 A | 8/1990 | Garcia | |
| D323,216 S | 1/1992 | Russell et al. | |
| D405,884 S | 2/1999 | Roper | |
| 5,944,016 A | 8/1999 | Ferko, III | |
| 6,227,201 B1 | 5/2001 | Ferko, III | |
| D656,234 S | 3/2012 | Keeney et al. | |
| D709,615 S | 7/2014 | Ruel et al. | |
| D819,219 S | 5/2018 | Izuka et al. | |
| D926,998 S | 8/2021 | Kosiorek et al. | |
| 2015/0094756 A1 | 4/2015 | Kosiorek et al. | |

FOREIGN PATENT DOCUMENTS

| | | |
|---|---|---|
| WO | 2016123652 A1 | 8/2016 |
| WO | 2019148012 A1 | 8/2019 |

OTHER PUBLICATIONS

"Communication pursuant to Rules 161 and 162 EPC received for EP Application No. 19744312.0 dated Sep. 15, 2020, pp. 3".

"Non-Final Office Action Received for U.S. Appl. No. 29/634,958, dated Aug. 23, 2019, 13 pages".

"Notice of Allowance received for U.S. Appl. No. 29/634,958, dated Apr. 14, 2021".

"Notice of Allowance Received for U.S. Appl. No. 29/634,958, dated Apr. 28, 2020, 08 pages".

"Extended European Search Report for European Application No. 19744312.0, Search completed on Sep. 21, 2021, dated Sep. 30, 2021.".

FIG. 12
FIG. 11
FIG. 13
FIG. 14

FIG. 39
FIG. 40
FIG. 41
FIG. 42

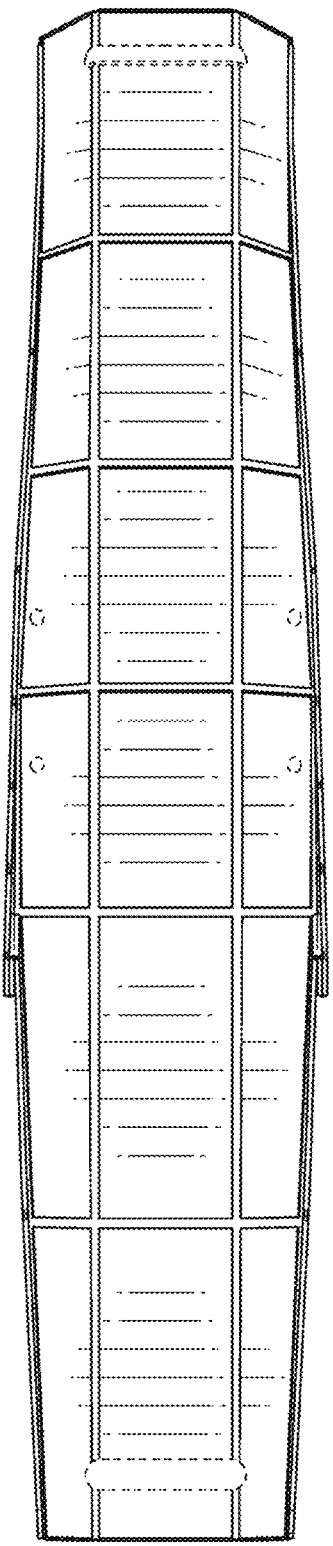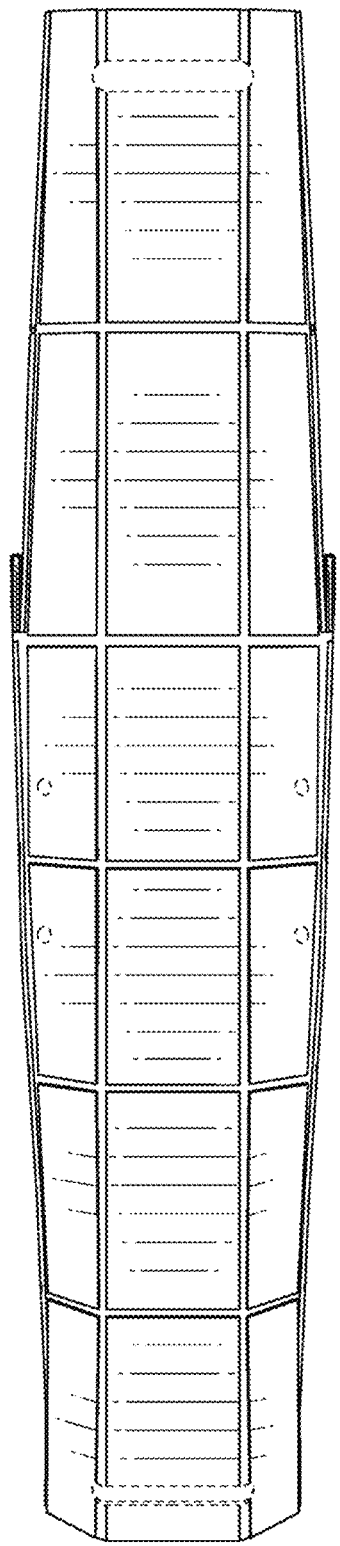
FIG. 55                    FIG. 56

RIGID IMMOBILIZATION SYSTEM FOR EXTREMITIES SPLINT APPARATUS, SYSTEMS AND METHODS

CROSS-REFERENCE TO RELATED APPLICATIONS

This application claims priority pursuant to 35 U.S.C. 119(e) to U.S. Provisional Patent Application Ser. No. 62/621,949, entitled "RIGID IMMOBILIZATION SYSTEM FOR EXTREMITIES SPLINT AND METHODS OF USE," filed Jan. 25, 2018, the entire disclosure of which is incorporated herein by reference.

FIELD

The present invention relates generally to medical devices and related systems and methods. More specifically, the present invention is concerned with a rigid immobilization system that is foldable for ease of storage and use.

BACKGROUND

Existing splints and other immobilization devices ("splints") are either too cumbersome and/or heavy when not in use or too flimsy when in use. Furthermore, existing splints do not provide the versatility required in the field, often requiring users to haul a variety of unnecessary pieces and/or components, increasing the risk that one or more such piece or component will be missing when needed. Furthermore still, many splint devices are designed for one-time use and/or can only be used feasibly a few times or less. Consequently, it would be beneficial to have a splint system that is lightweight and durable. Furthermore, it would be beneficial if the splint were capable of being easily moved between a stowed configuration for ease of storage and a variety of rigid deployed configuration for use. Furthermore still, it would be beneficial if the split were formed from a material and with a configuration so as to facilitate multiple uses and to minimize loss of any necessary pieces or components.

SUMMARY

The present inventive concept is an immobilization device. It includes an elongated main body and two or more panels with a living hinge between each panel. Each panel also includes two or more segments with a living hinge between each segment. The main body is moveable between multiple configurations. In the flat configuration, the panels and segments are all unfolded and flat relative to one another. In the stowable configuration, the panels are folded over one another to minimize the surface area of the main body. The main body may also be moved to various deployed configurations. In each deployed configuration, the angle between two adjacent panels is at or between 0 and 180 degrees. In each deployed configuration, the outermost segments of each panel are folded at an angle between 0 and 180 degrees with respect to the next adjacent segment of that panel. Folding along the hinges between segments provides strength and rigidity to the device in the lengthwise direction when the device is in the various deployed configurations.

In some embodiments, the main body includes one or more hole or slot, sized and shaped such that they align when the main body is folded into the stowable configuration. The holes may also be sized and shaped to receive a strap, band, cord, cable, nail, pin, or other fastener. The fastener through the holes secures the device in the stowable configuration or the deployed configuration. In some embodiments, the immobilization device is configured to be used with a tourniquet such that compressive loads are distributed across a larger area than is possible through the use of a tourniquet alone, such as a pelvic binder. Sometimes, the device is used with a tourniquet where the tourniquet is the fastener securing the device in place.

The device in each deployed configuration is configured to restrain an appendage, limb, or extremity in various different predetermined positions, such as 180 degree orientation (straight arm or leg), 45 degrees, 90 degrees, 135 degrees, etc. The main body includes one or more pinch point configured to establish and maintain these various different predetermined angles.

The foregoing and other objects are intended to be illustrative of the invention and are not meant in a limiting sense. Many possible embodiments of the invention may be made and will be readily evident upon a study of the following specification and accompanying drawings comprising a part thereof. Various features and subcombinations of invention may be employed without reference to other features and subcombinations. Other objects and advantages of this invention will become apparent from the following description taken in connection with the accompanying drawings, wherein is set forth by way of illustration and example, an embodiment of this invention and various features thereof.

BRIEF DESCRIPTION OF THE DRAWINGS

A preferred embodiment of the present inventive concept, illustrative of the best mode in which the applicant has contemplated applying the principles, is set forth in the following description and is shown in the drawings and is particularly and distinctly pointed out and set forth in the appended claims.

FIG. 11 is a first end view of the embodiment shown in FIG. 8.

FIG. 12 is a second end view of the embodiment shown in FIG. 8.

FIG. 13 is a first side view of the embodiment shown in FIG. 8.

FIG. 14 is a second side view of the embodiment shown in FIG. 8.

FIG. 39 is a first end view of the embodiment shown in FIG. 36.

FIG. 40 is a second end view of the embodiment shown in FIG. 36.

FIG. 41 is a first side view of the embodiment shown in FIG. 36.

FIG. 42 is a second side view of the embodiment shown in FIG. 36.

FIG. 55 is a top view of the embodiment shown in FIG. 50.

FIG. 56 is a bottom view of the embodiment shown in FIG. 50.

DETAILED DESCRIPTION

Figure 1:
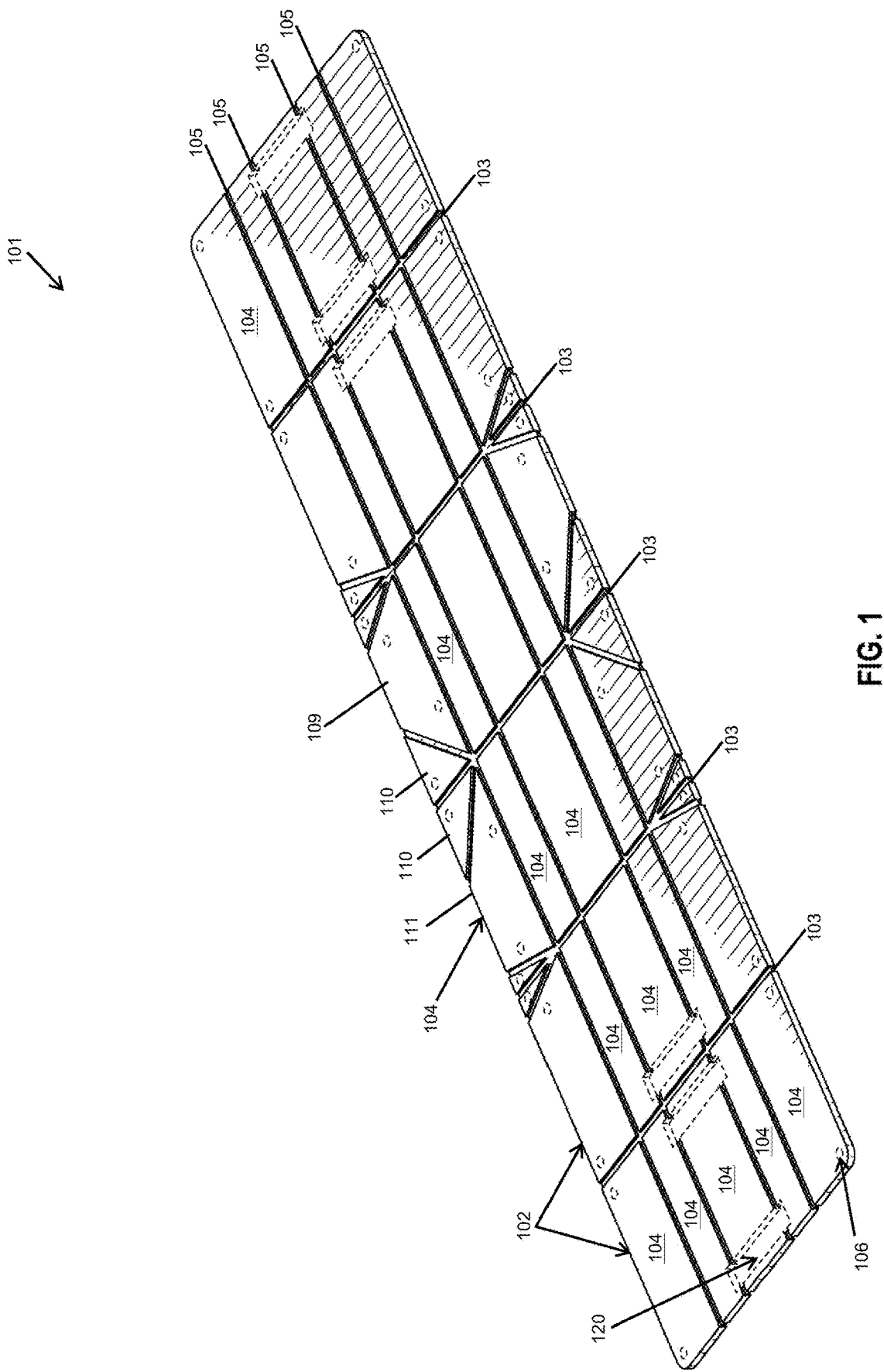
FIG. 1 is a perspective view of a first embodiment of an immobilization device of the present invention, the main body shown in a flat configuration, broken lines showing of holes and slots through the main body are for the purpose of showing additional optional embodiments.
Figure 2:
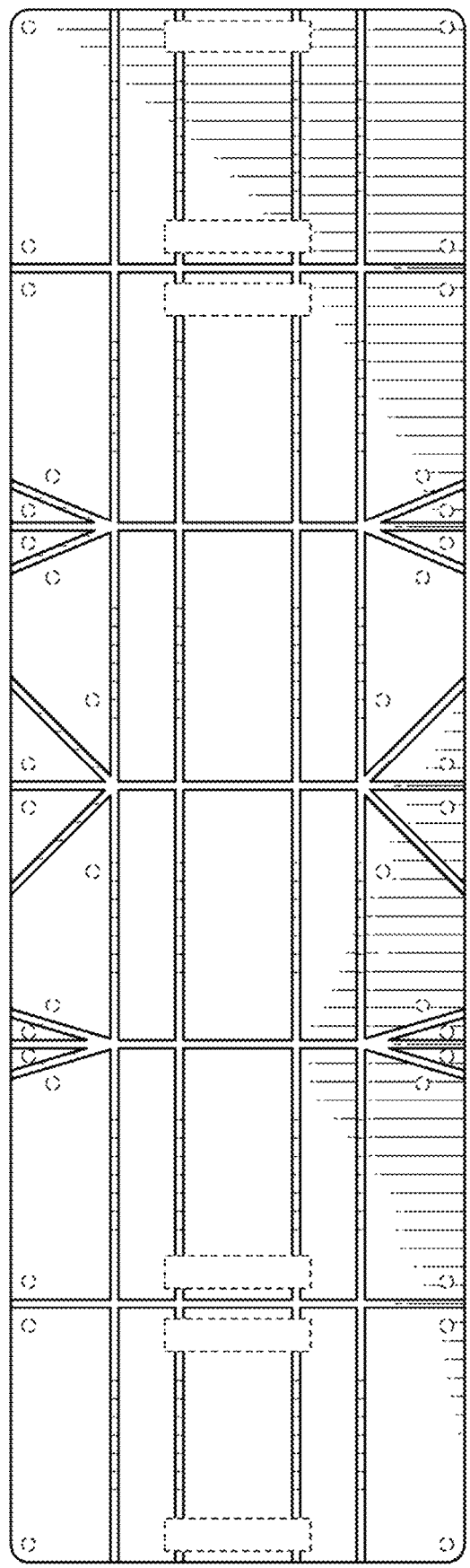
FIG. 2 is a front view of the embodiment shown in FIG. 1.
Figure 3:
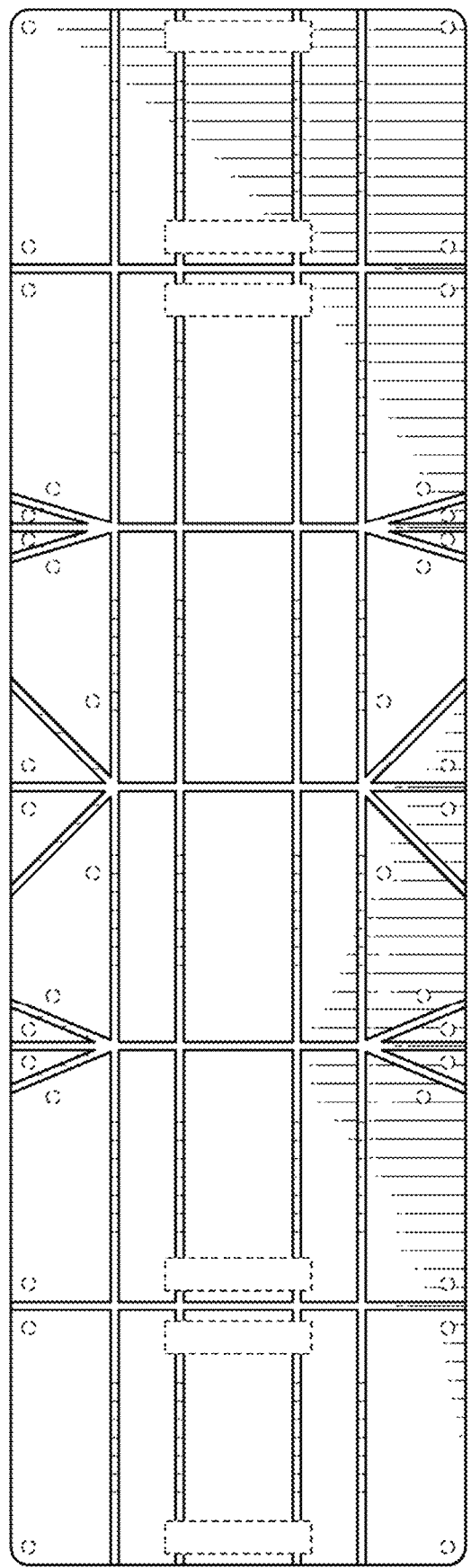
FIG. 3 is a rear view of the embodiment shown in FIG. 1.
Figures 4, 5, 6, 7:
FIG. 4 is a first end view of the embodiment shown in FIG. 1.
FIG. 5 is a second end view of the embodiment shown in FIG. 1.
FIG. 6 is a first side view of the embodiment shown in FIG. 1.
FIG. 7 is a second side view of the embodiment shown in FIG. 1.
Figure 8:
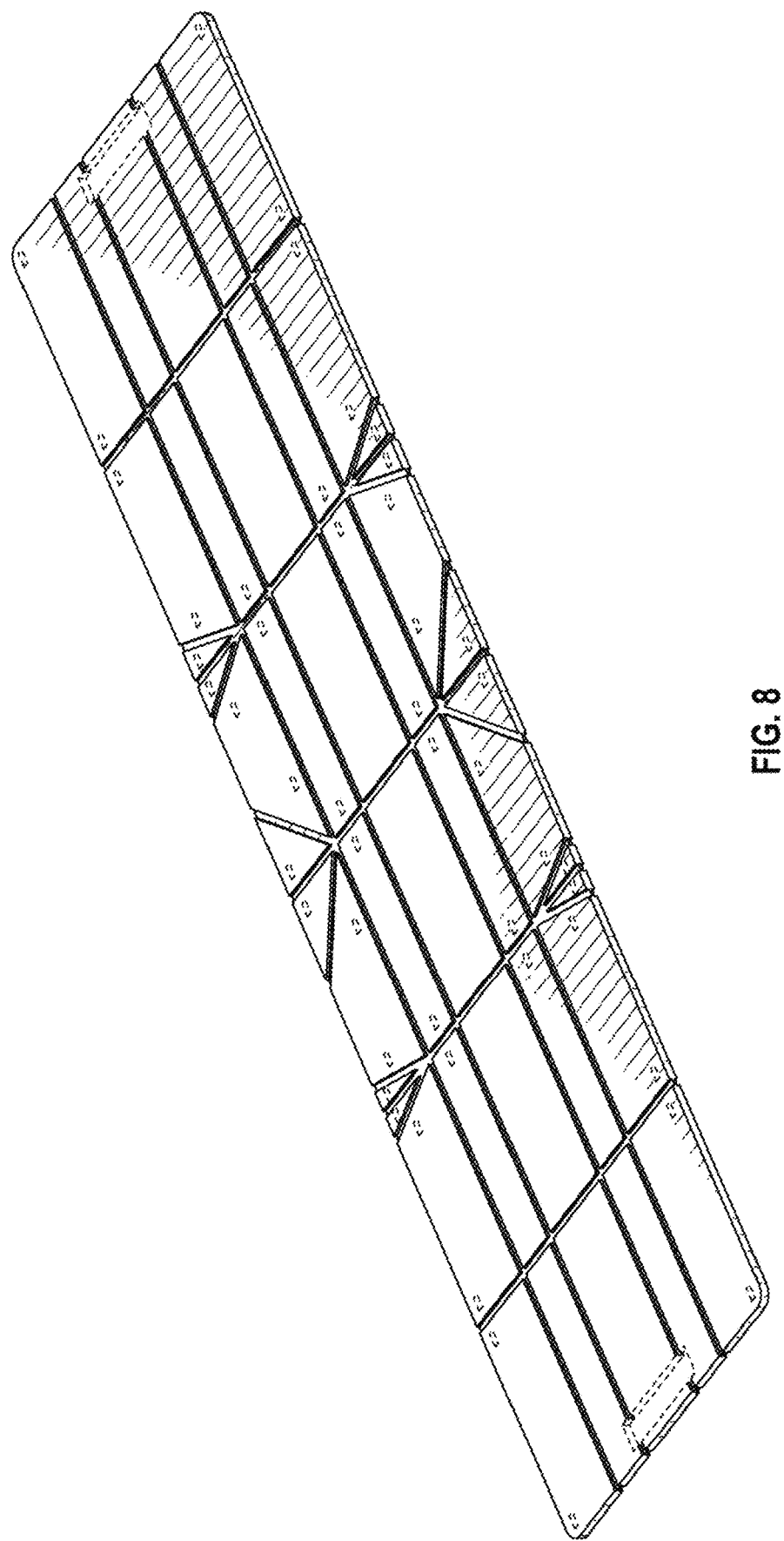
FIG. 8 is a perspective view of a second embodiment of an immobilization device of the present invention, the main body shown in a flat configuration, broken lines showing of large and small slots through the main body are for the purpose of showing additional optional embodiments.
Figure 9:
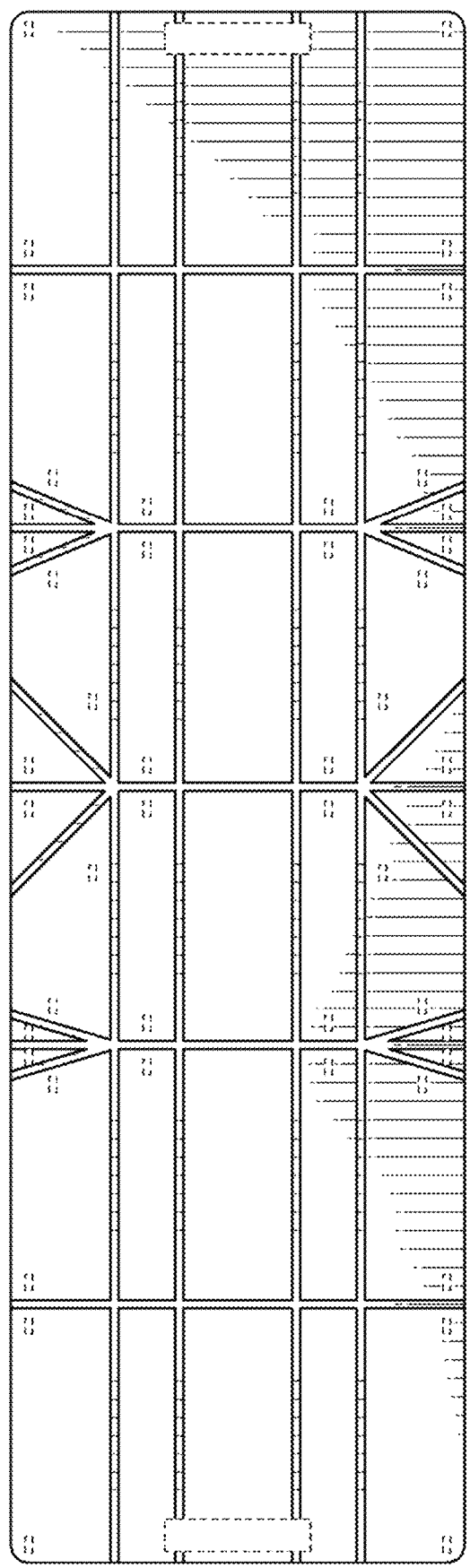
FIG. 9 is a front view of the embodiment shown in FIG. 8.
Figure 10:
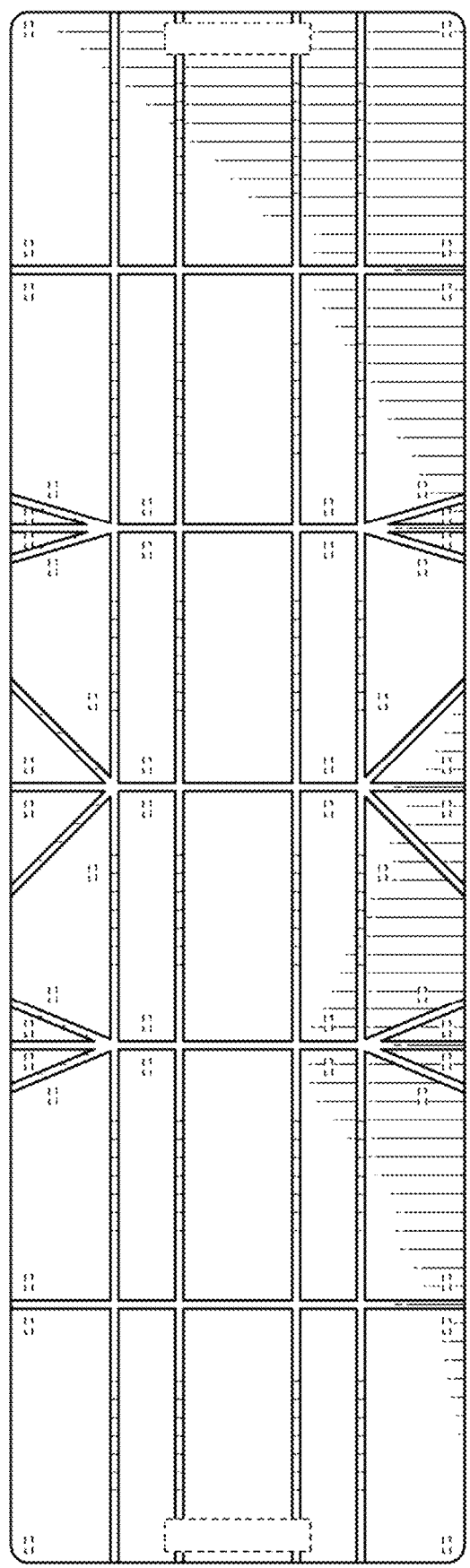
FIG. 10 is a rear view of the embodiment shown in FIG. 8.
Figure 15:
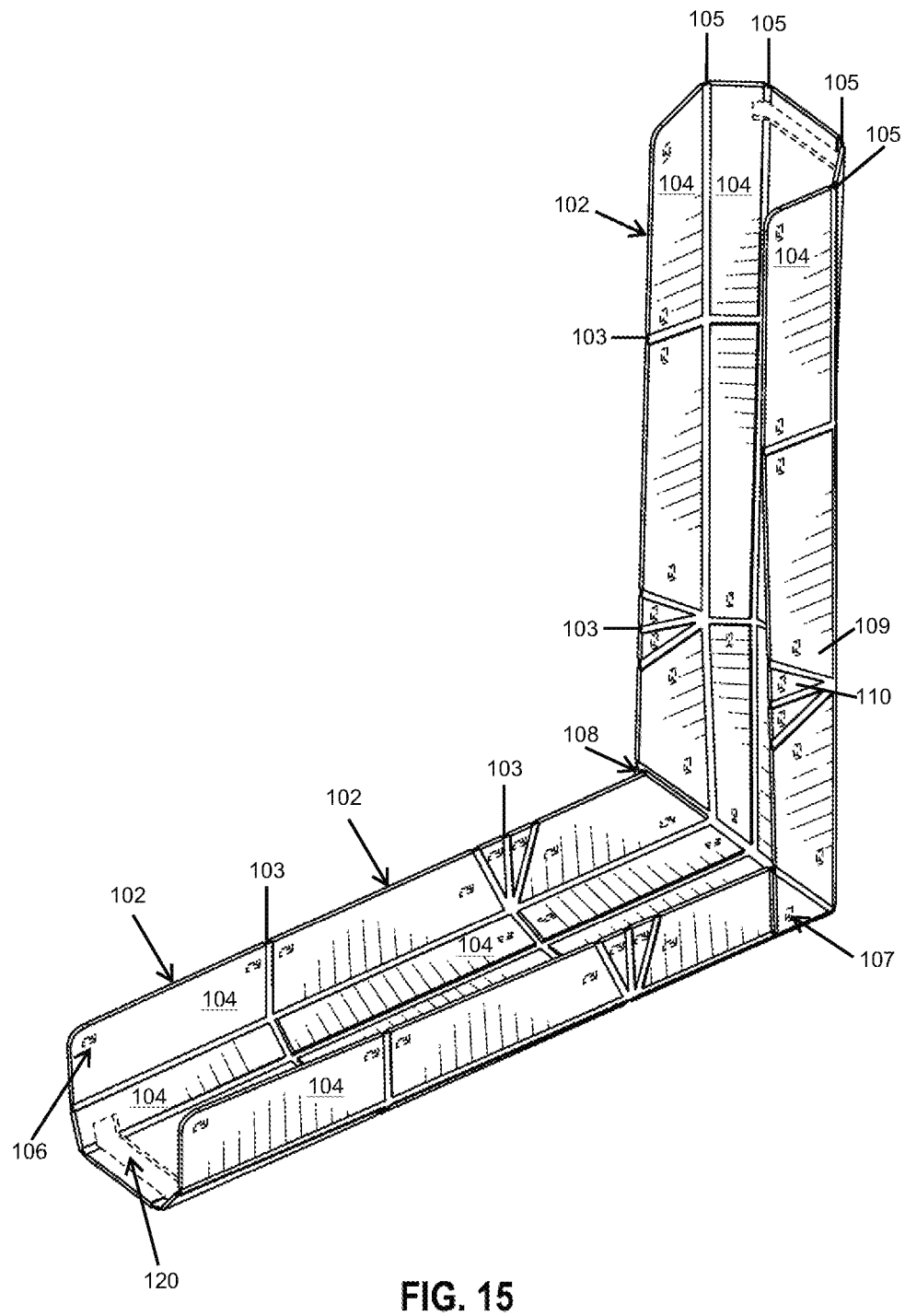
FIG. 15 is a perspective view of the embodiment shown in FIG. 8, the main body shown in a first deployed configuration with a first portion of the main body being generally perpendicular to a second portion of the main body.
Figure 16:
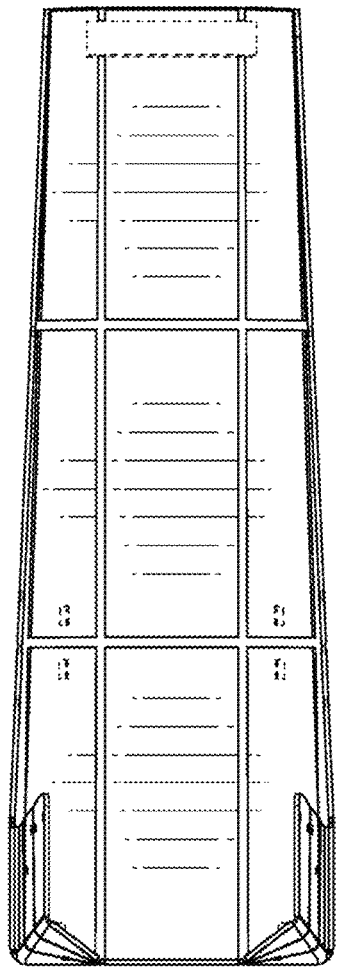
FIG. 16 is a front view of the embodiment shown in FIG. 15.
Figure 17:
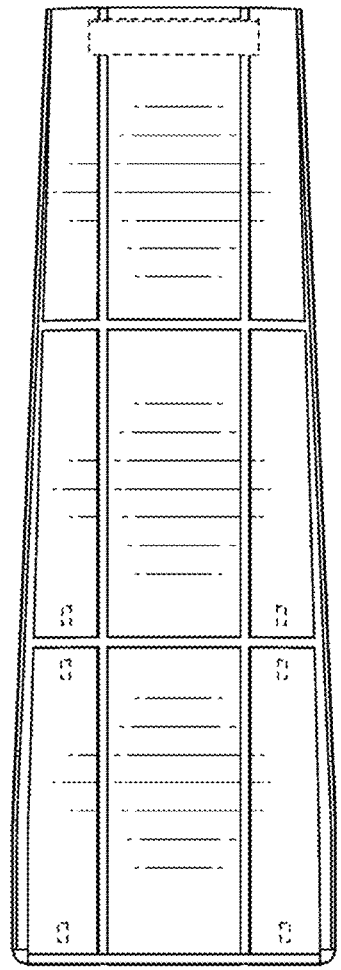
FIG. 17 is a rear view of the embodiment shown in FIG. 15.
Figure 18:
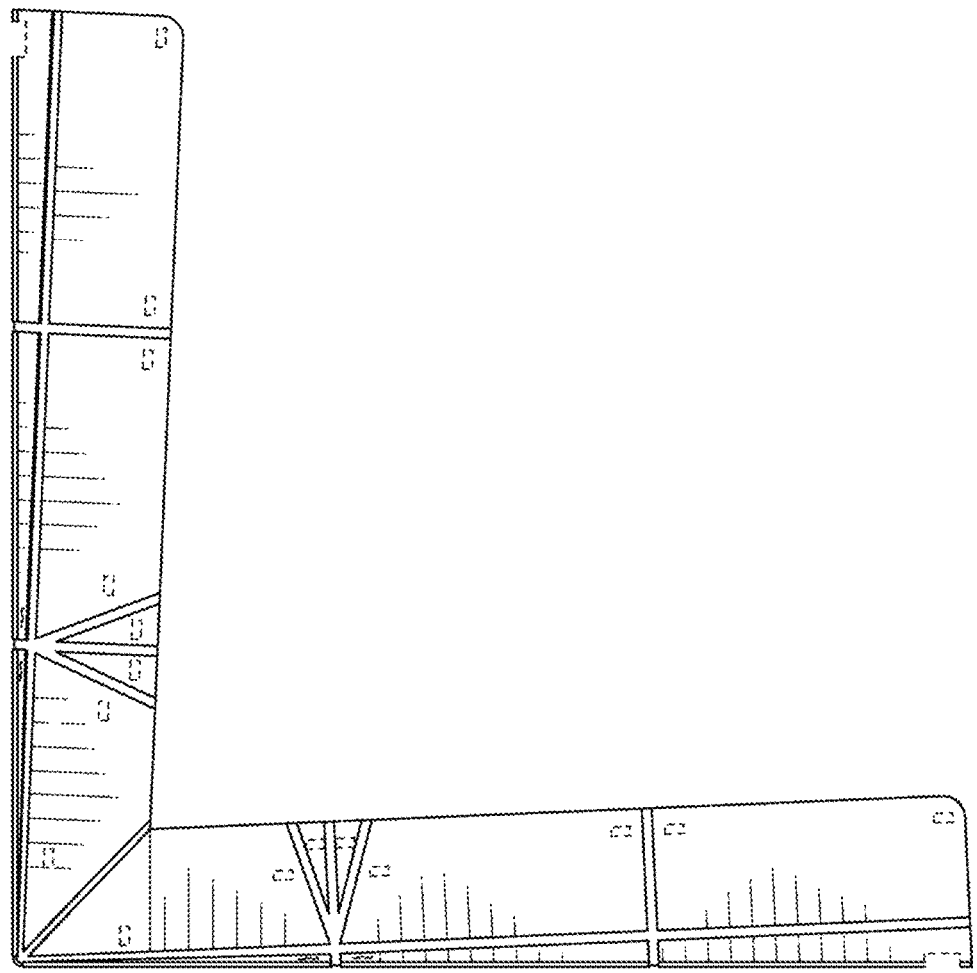
FIG. 18 is a first side view of the embodiment shown in FIG. 15.
Figure 19:
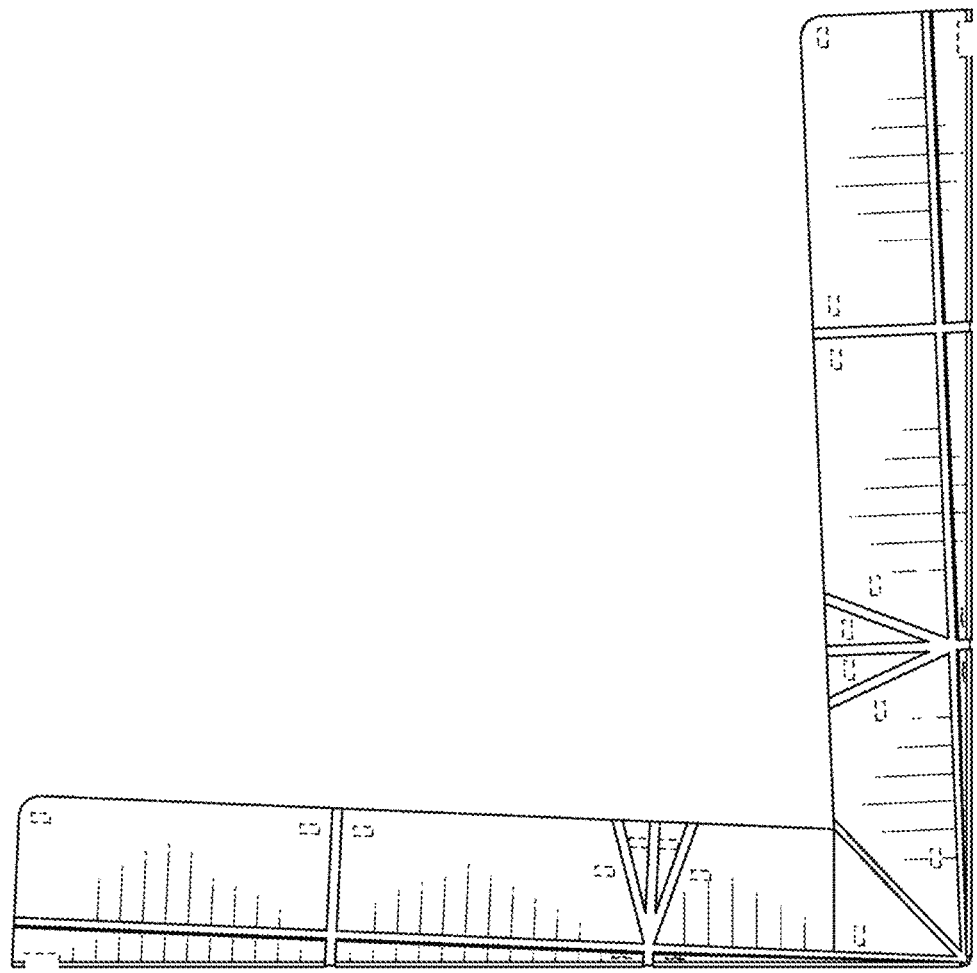
FIG. 19 is a second side view of the embodiment shown in FIG. 15.
Figure 20:
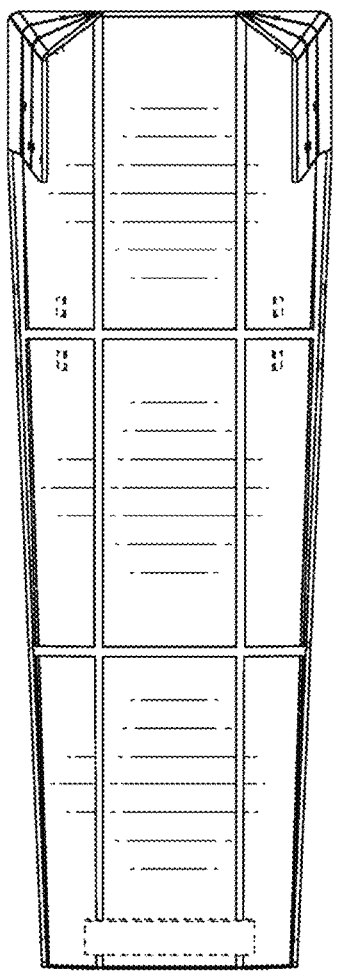
FIG. 20 is a top view of the embodiment shown in FIG. 15.
Figure 21:
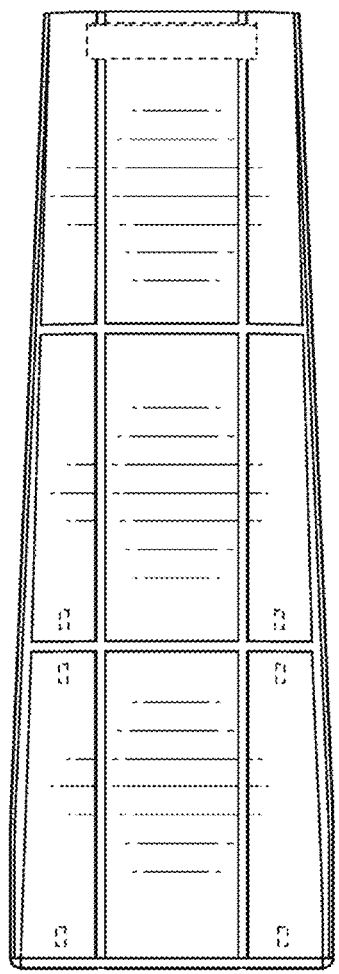
FIG. 21 is a bottom view of the embodiment shown in FIG. 15.
Figure 22:
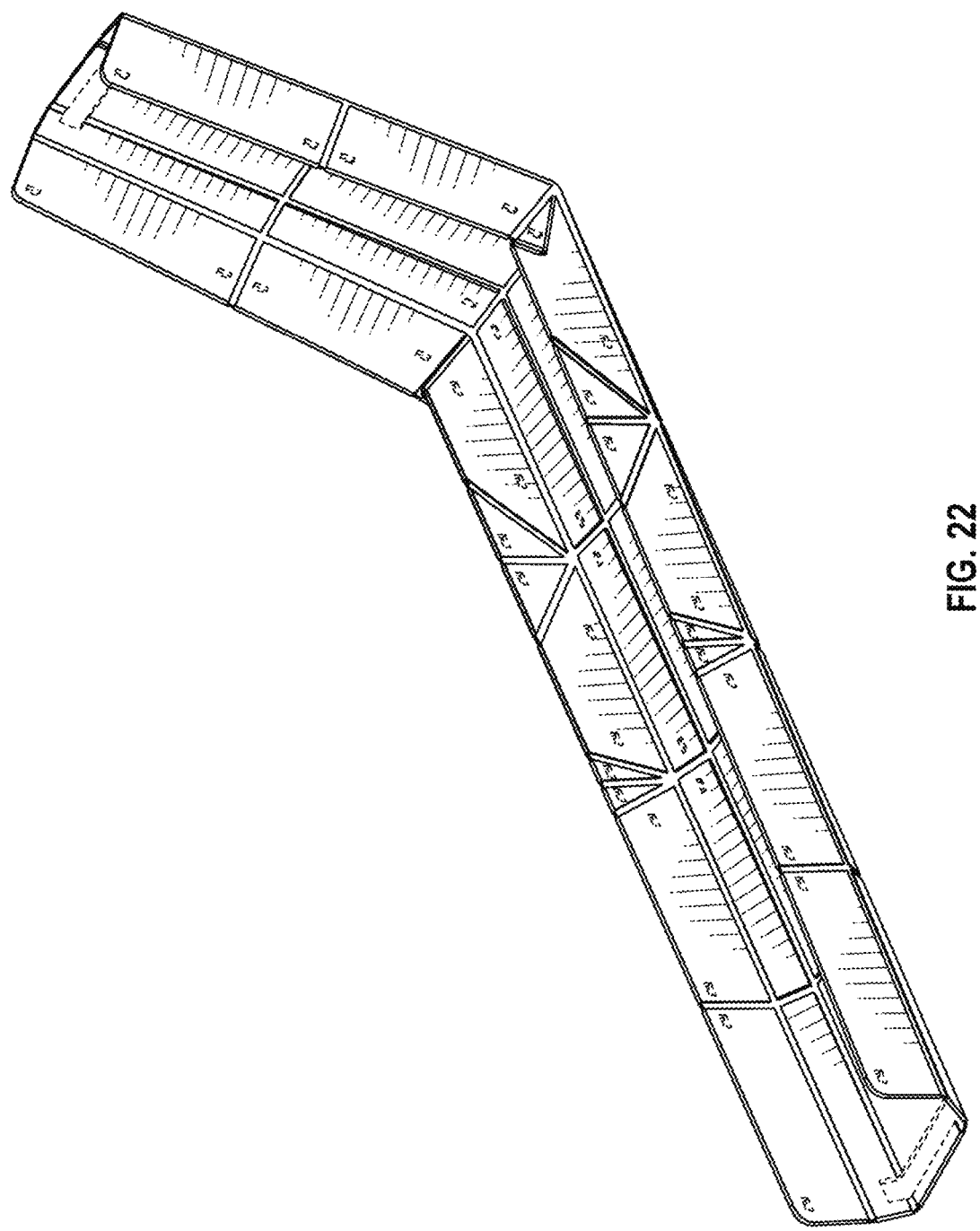
FIG. 22 is a perspective view of the embodiment shown in FIG. 8, the main body shown in a second deployed configuration with a first portion of the main body being angled away from a second portion of the main body.
Figure 23:
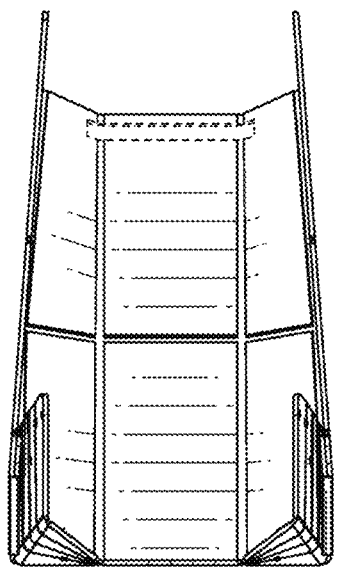
FIG. 23 is a front view of the embodiment shown in FIG. 22.
Figure 24:
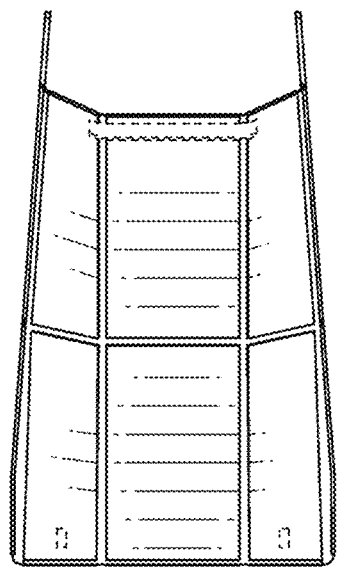
FIG. 24 is a rear view of the embodiment shown in FIG. 22.
Figure 25:
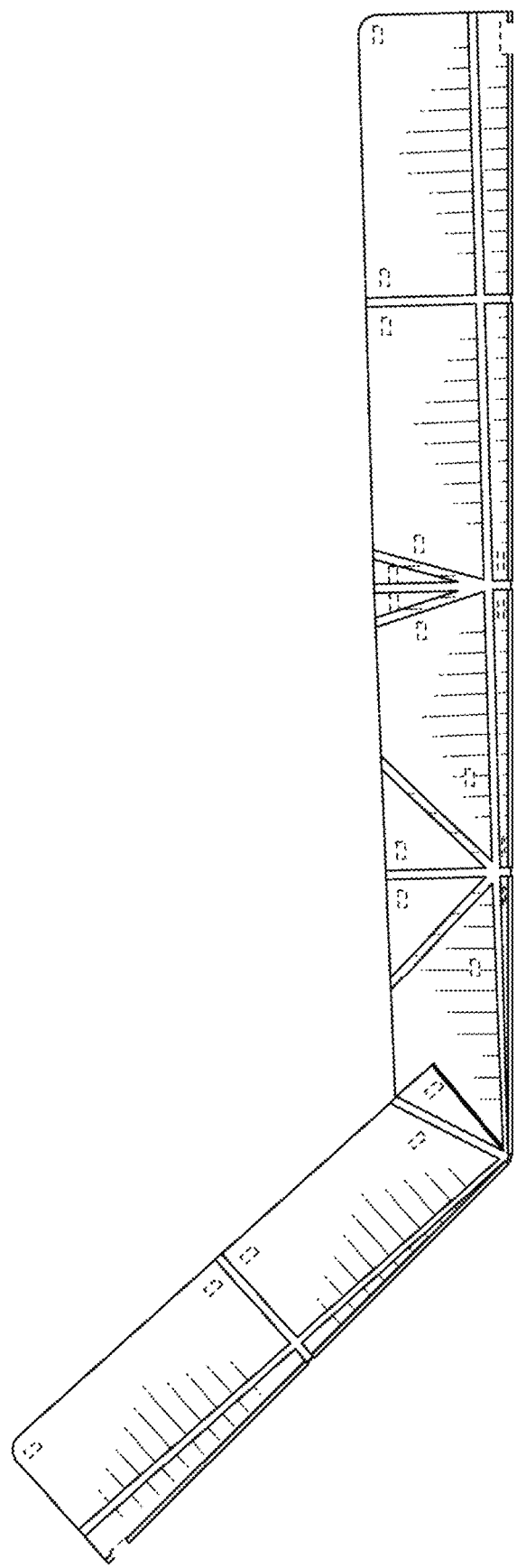
FIG. 25 is a first side view of the embodiment shown in FIG. 22.
Figure 26:
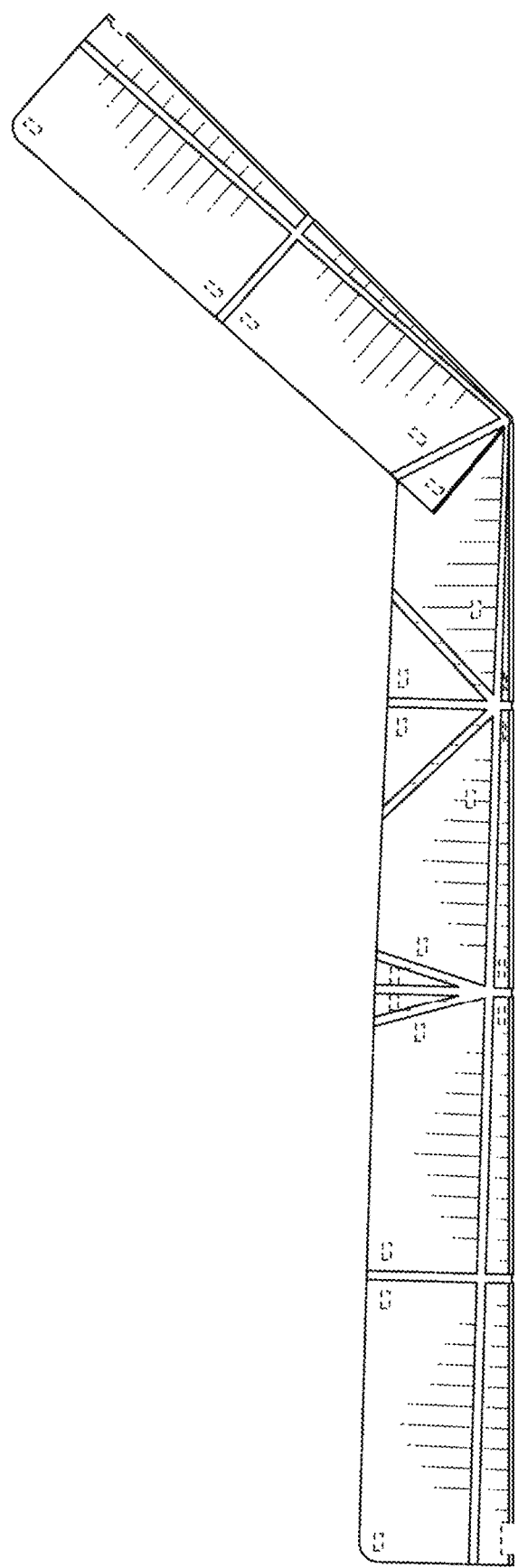
FIG. 26 is a second side view of the embodiment shown in FIG. 22.
Figure 27:
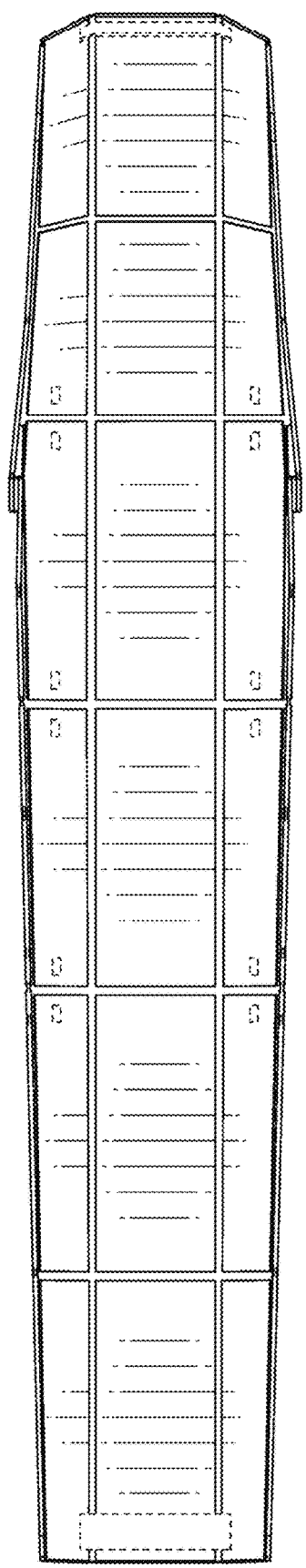
FIG. 27 is a top view of the embodiment shown in FIG. 22.
Figure 28:
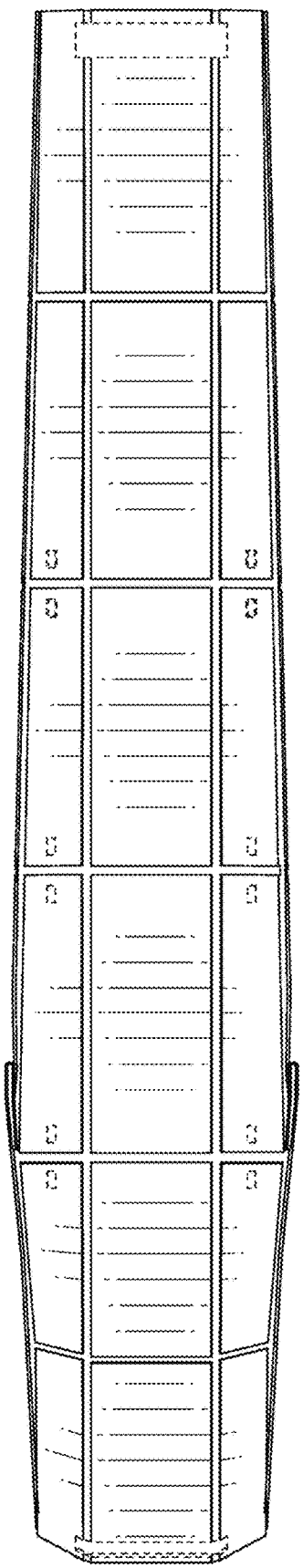
FIG. 28 is a bottom view of the embodiment shown in FIG. 22.
Figure 29:
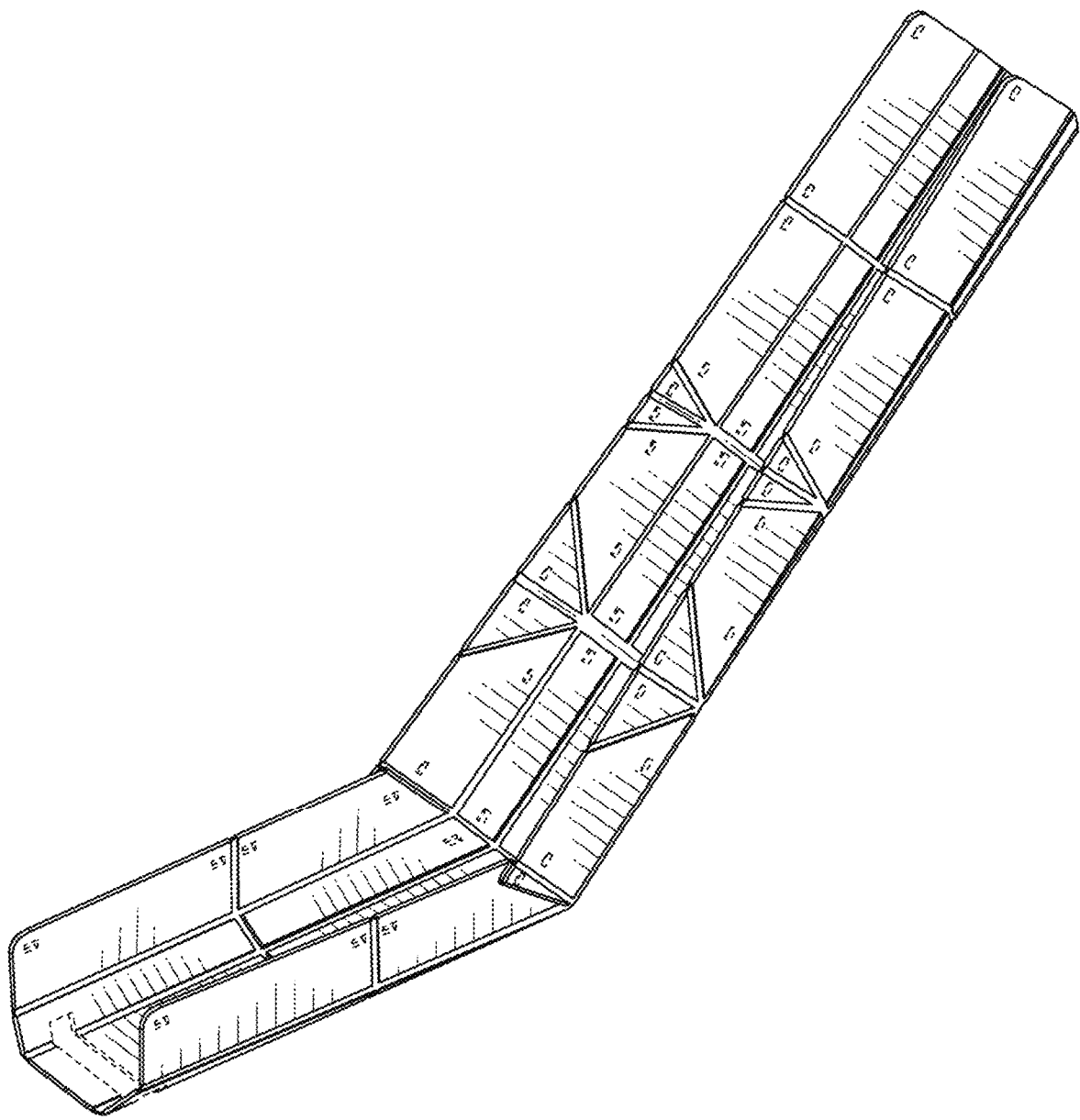
FIG. 29 is a perspective view of the embodiment shown in FIG. 8, the main body shown in a third deployed configuration with a first portion of the main body being angled away from a second portion of the main body.
Figure 30:
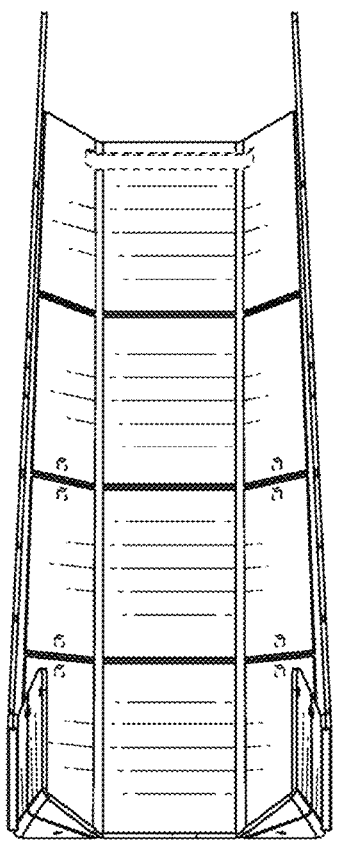
FIG. 30 is a front view of the embodiment shown in 29.
Figure 31:
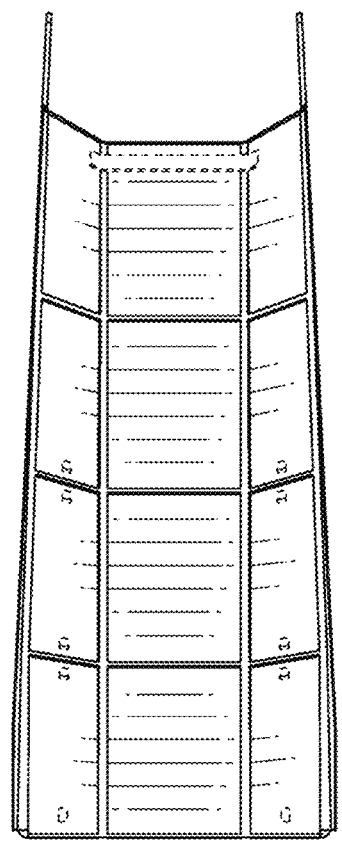
FIG. 31 is a rear view of the embodiment shown in 29.
Figure 32:
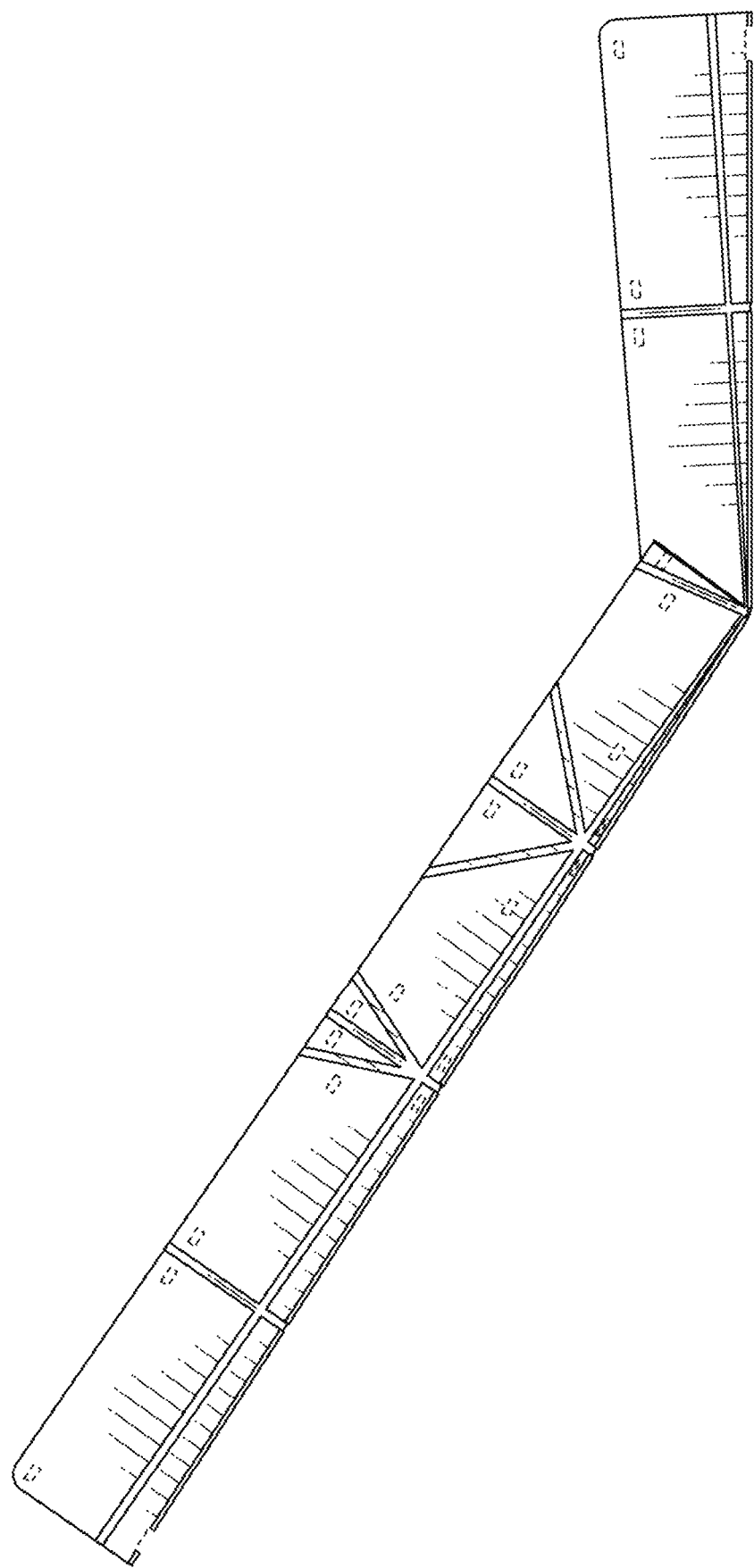
FIG. 32 is a first side view of the embodiment shown in 29.
Figure 33:
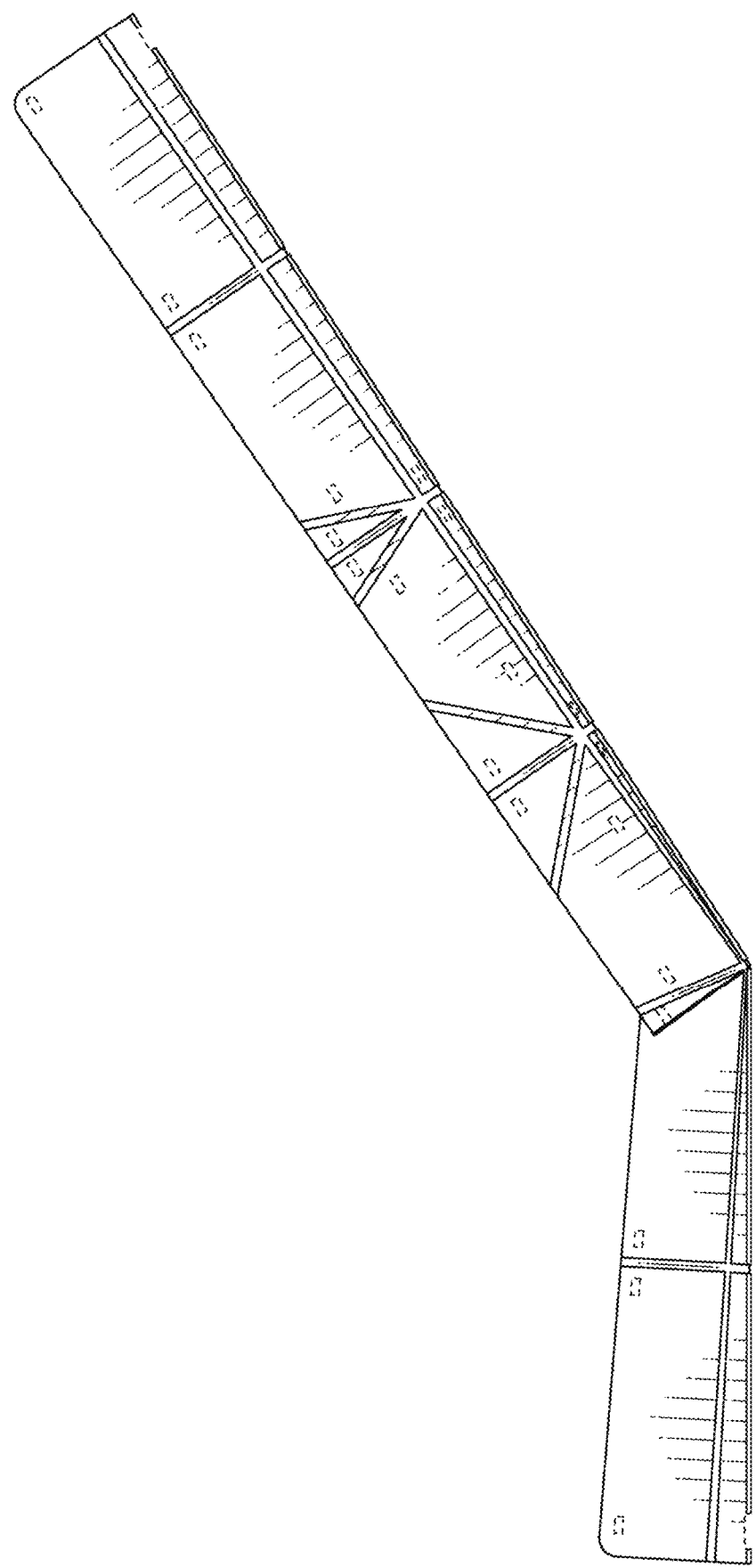
FIG. 33 is a second side view of the embodiment shown in 29.
Figure 34:
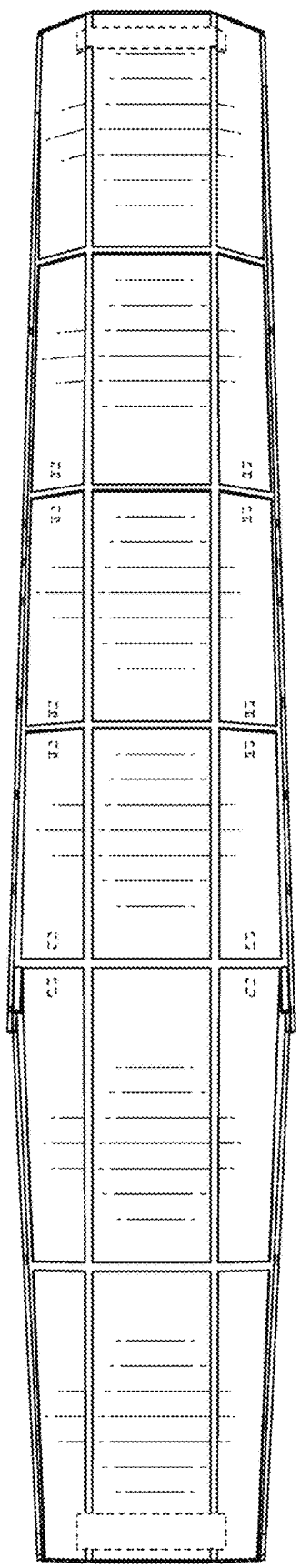
FIG. 34 is a top view of the embodiment shown in 29.
Figure 35:
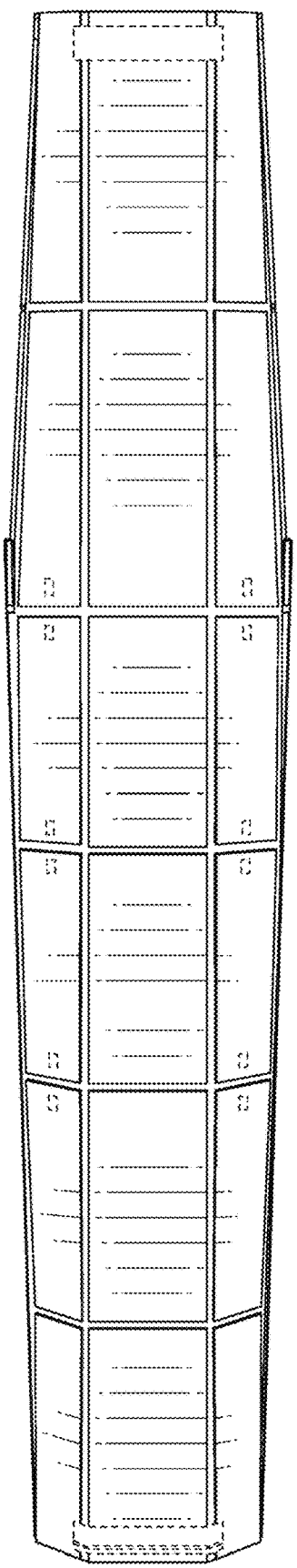
FIG. 35 is a bottom view of the embodiment shown in 29.
Figure 36:
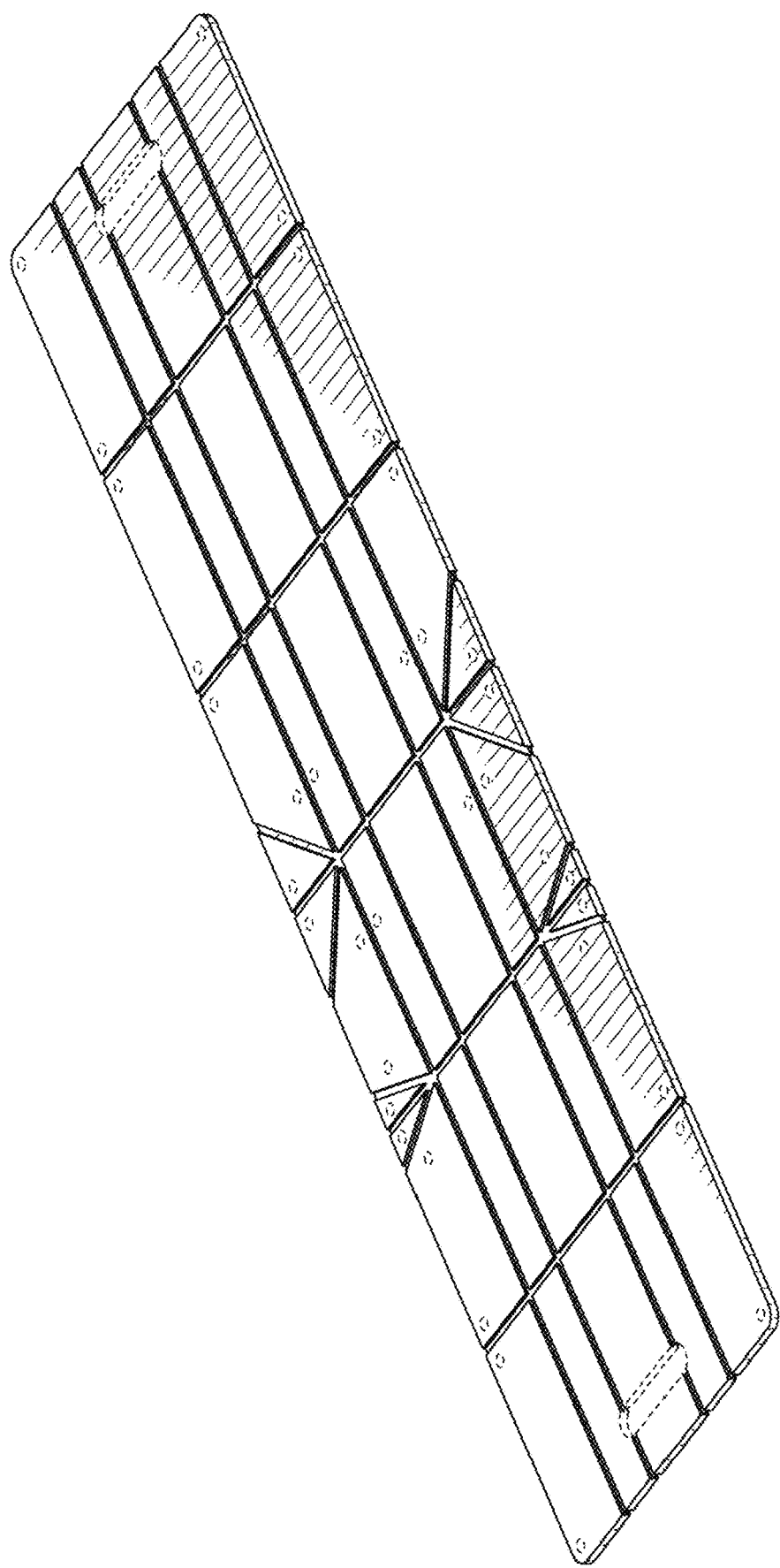
FIG. 36 is a perspective view of a third embodiment of an immobilization device of the present invention, the main body shown in a flat configuration, broken lines showing of holes and slots through the main body are for the purpose of showing additional optional embodiments.
Figure 37:
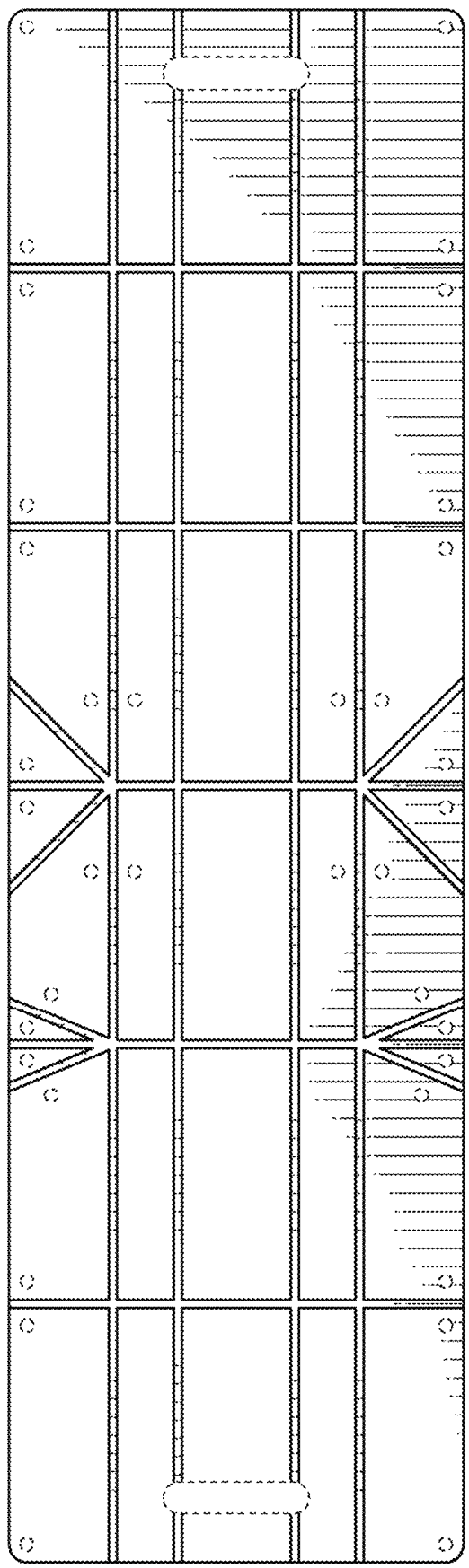
FIG. 37 is a front view of the embodiment shown in FIG. 36.
Figure 38:
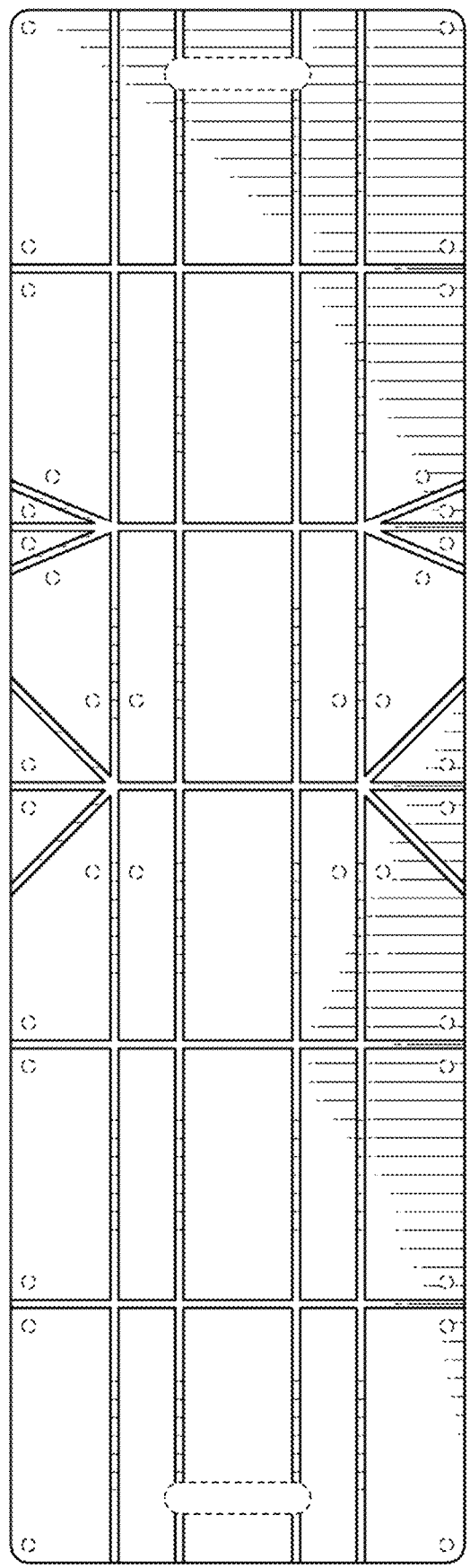
FIG. 38 is a rear view of the embodiment shown in FIG. 36.
Figure 43:
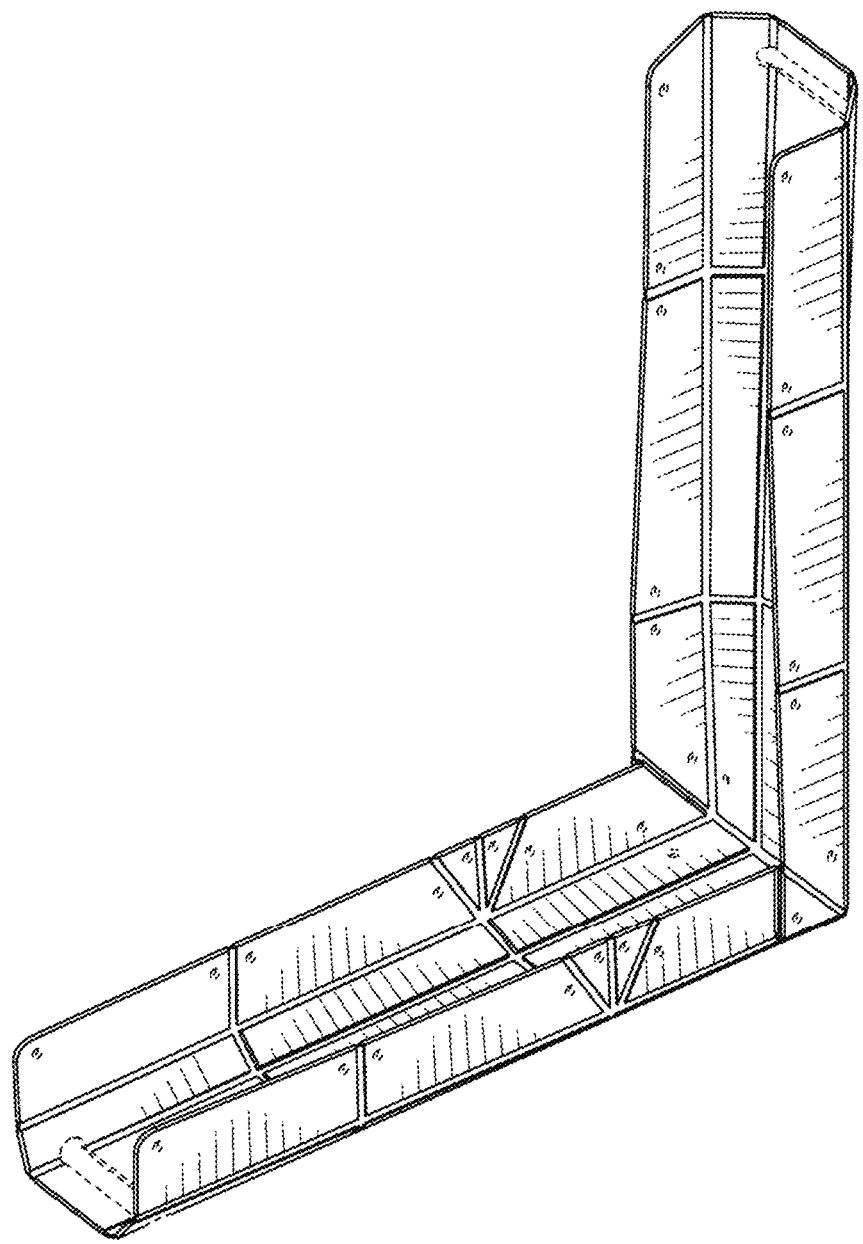
FIG. 43 is a perspective view of the embodiment shown in FIG. 36, the main body shown in a first deployed configuration with a first portion of the main body being generally perpendicular to a second portion of the main body.
Figure 44:
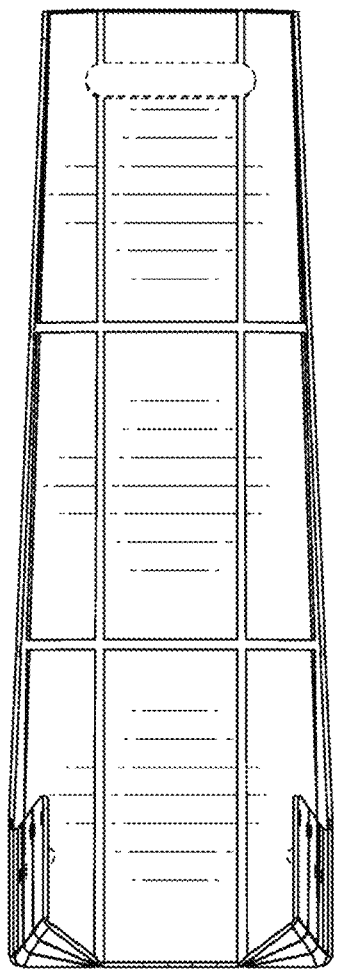
FIG. 44 is a front view of the embodiment shown in FIG. 43.
Figure 45:
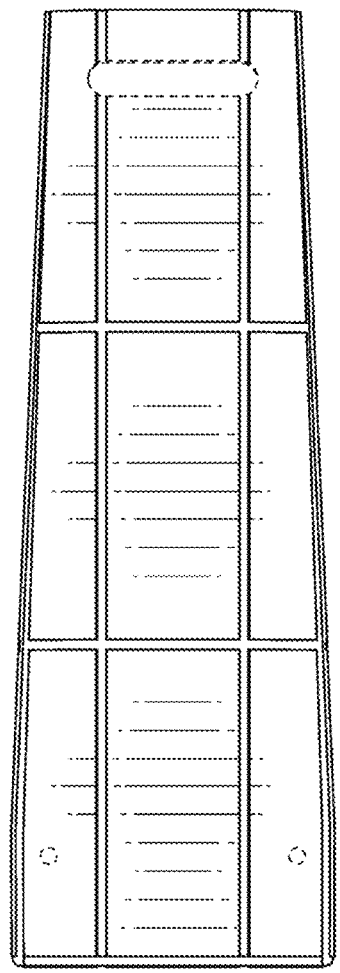
FIG. 45 is a rear view of the embodiment shown in FIG. 43.
Figure 46:
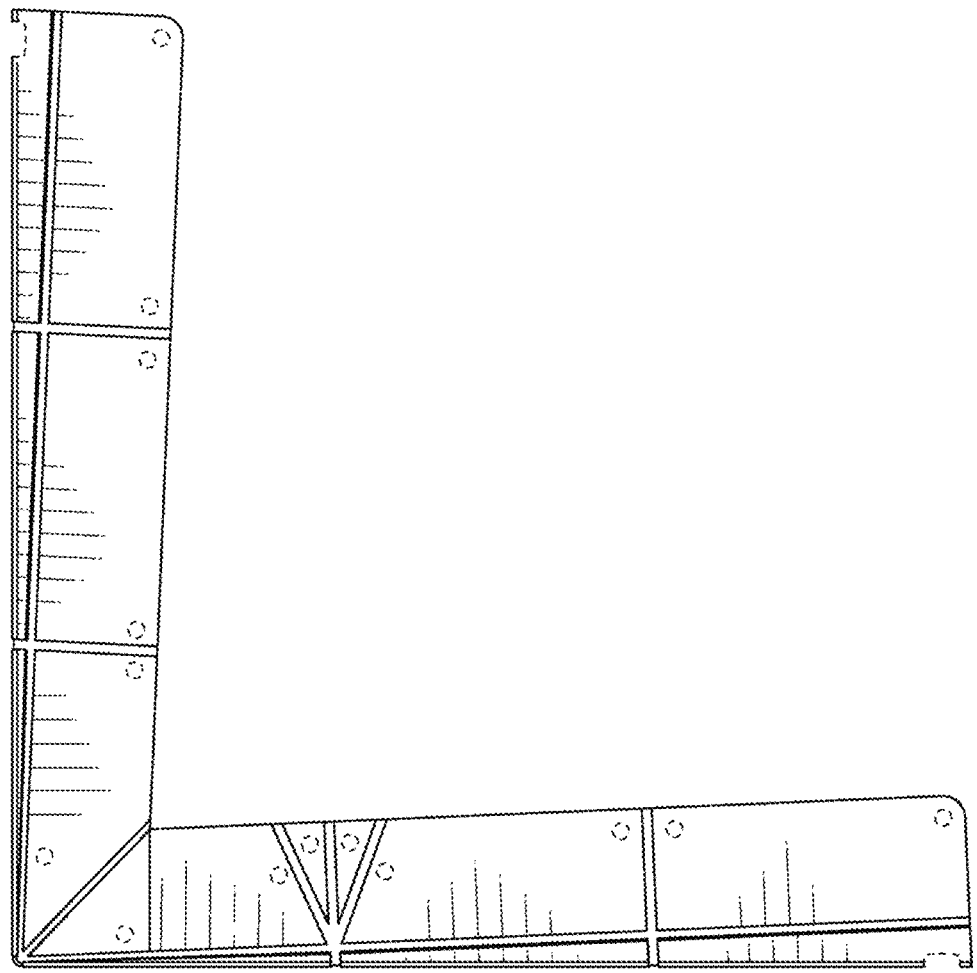
FIG. 46 is a first side view of the embodiment shown in FIG. 43.
Figure 47:
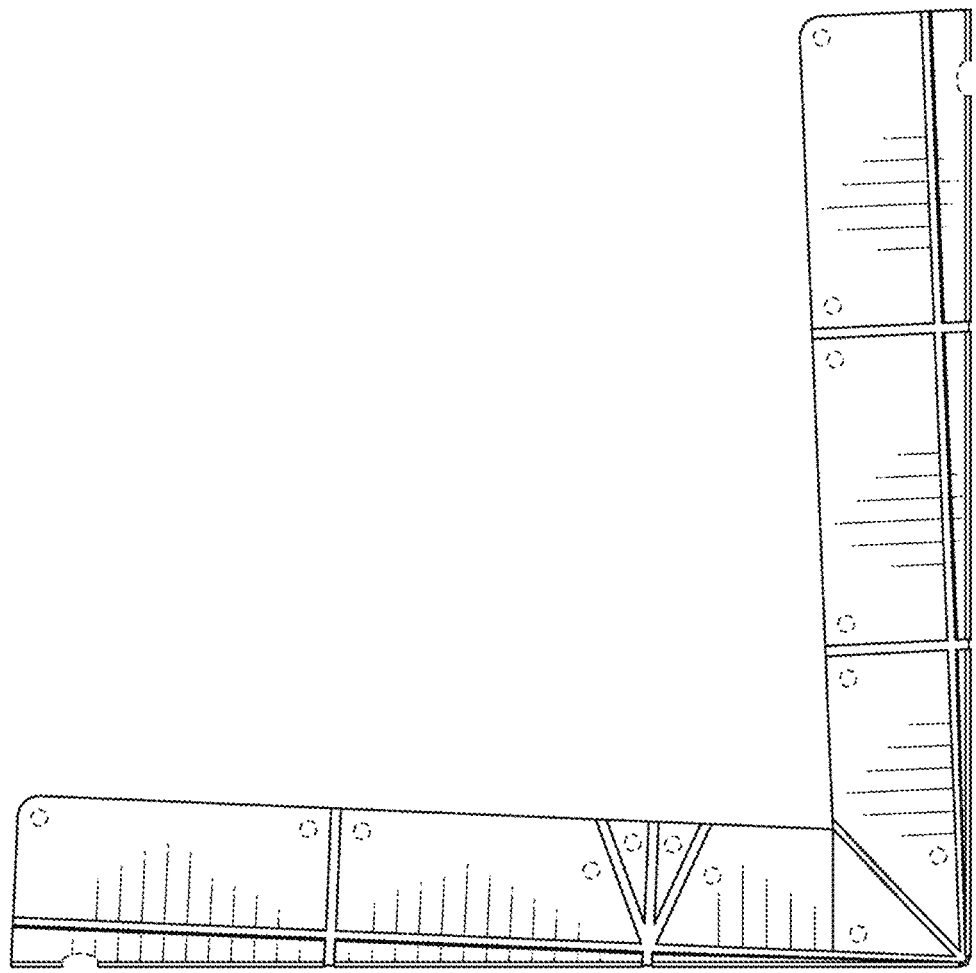
FIG. 47 is a second side view of the embodiment shown in FIG. 43.
Figure 48:
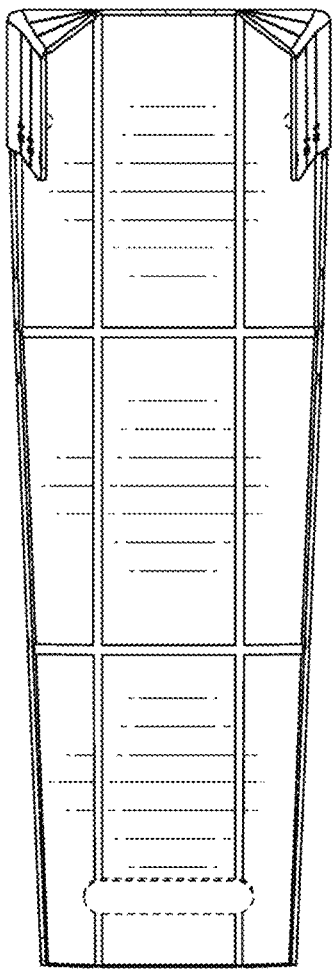
FIG. 48 is a top view of the embodiment shown in FIG. 43.
Figure 49:
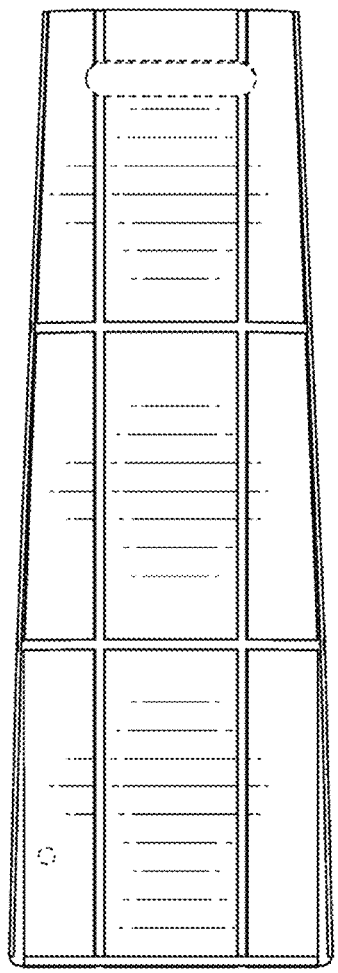
FIG. 49 is a bottom view of the embodiment shown in FIG. 43.
Figure 50:
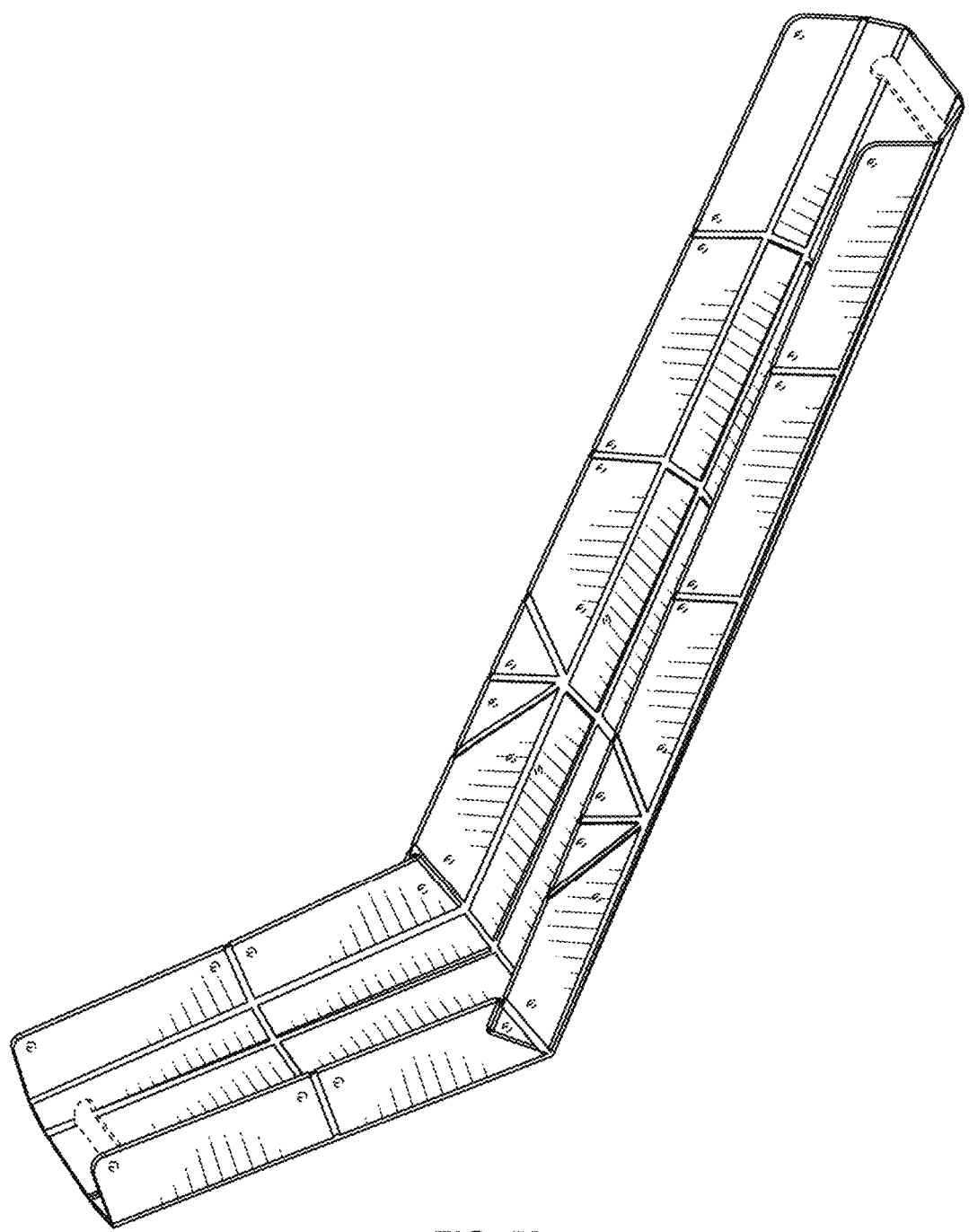
FIG. 50 is a perspective view of the embodiment shown in FIG. 36, the main body shown in a second deployed configuration with a first portion of the main body being angled away from a second portion of the main body.
Figure 51:
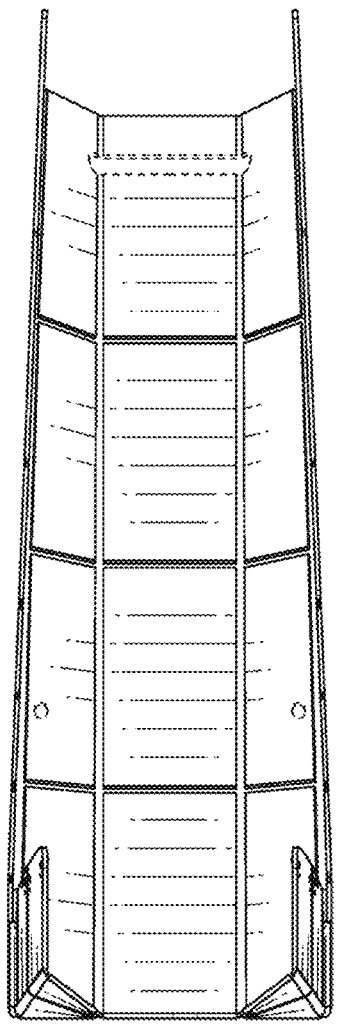
FIG. 51 is a front view of the embodiment shown in FIG. 50.
Figure 52:
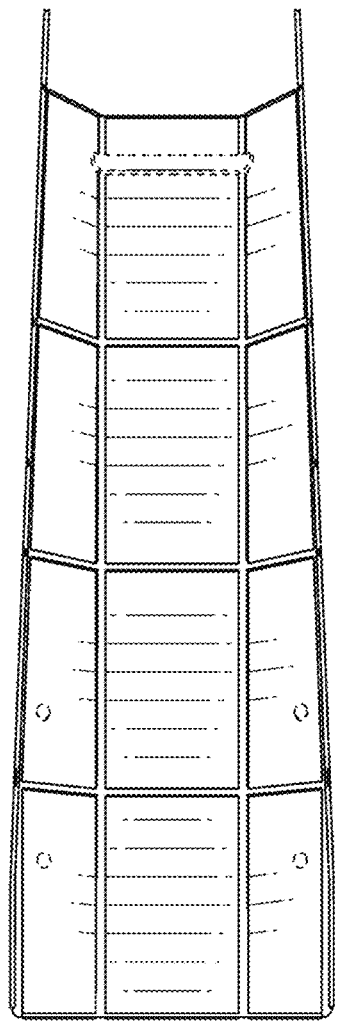
FIG. 52 is a rear view of the embodiment shown in FIG. 50.
Figure 53:
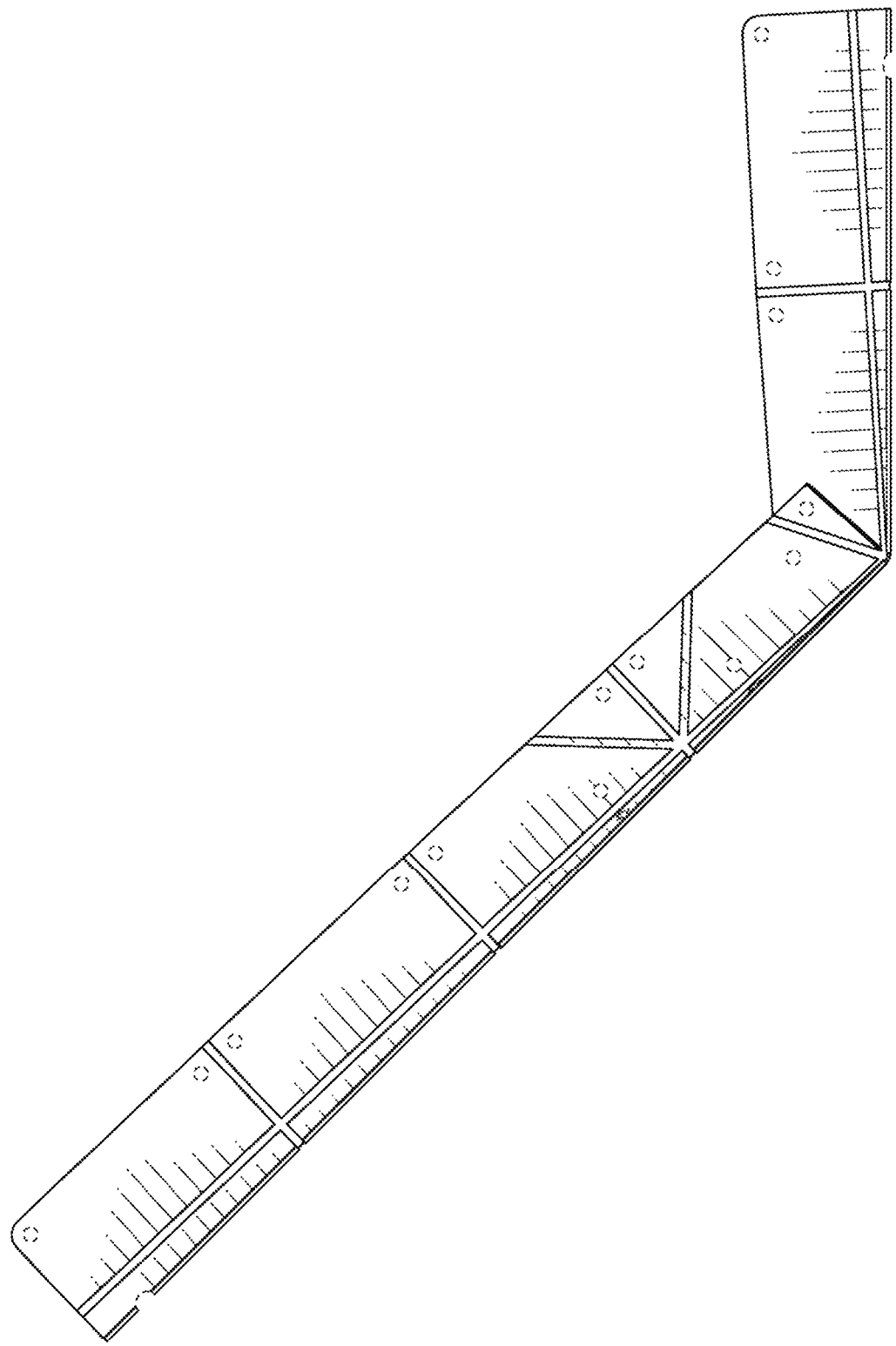
FIG. 53 is a first side view of the embodiment shown in FIG. 50.
Figure 54:
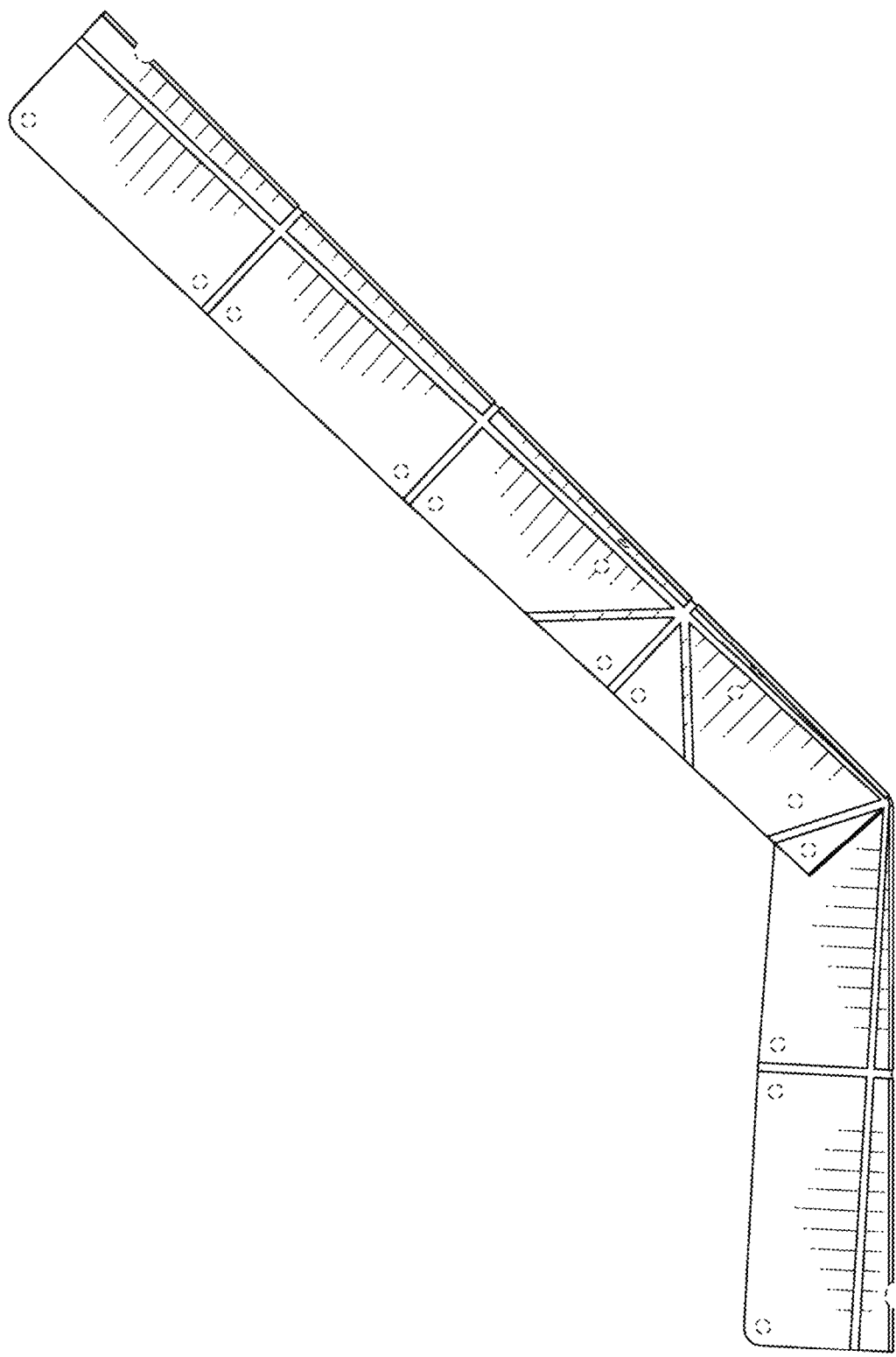
FIG. 54 is a second side view of the embodiment shown in FIG. 50.

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

In some embodiments, the present inventive concept is an immobilization device 10. The immobilization device is used to splint or immobilize a bodily extremity. The immobilization device includes an elongated main body 101. The main body includes a plurality of panels 102 with a hinged panel connection 103 between each panel and its adjacent panel(s). Each panel includes a plurality of segments 104 with a hinged segment connection 105 between each segment and its adjacent segment(s). In some embodiments, a panel connection angle is defined by the geometric angle between two adjacent panels. In some embodiments, a segment connection angle is defined by the geometric angle between two adjacent segments. In some embodiments, the hinged panel connection is a living hinge. In some embodiments, the hinged segment connection is a living hinge. In some embodiments, the entire main body is formed of a single piece of material and the hinged panel connection(s) and the hinged segment connection(s) are living hinges. In some embodiments, the main body is formed from metal, polypropylene, polyethylene, or other plastics.

Referring to FIGS. 1-14 and 36-42, in some embodiments, the main body is unfolded into a flat configuration. Each panel is unfolded and flat with respect to its adjacent panel(s). In the flat configuration, the panel connection angle is 180 degrees. In other words, the panels are all aligned and parallel in the flat configuration. In the flat configuration, the segment connection angle is 180 degrees. In other words, the segments within each panel remain flat with respect to one another and also with respect to the segments of adjacent panels.

Figure 57:
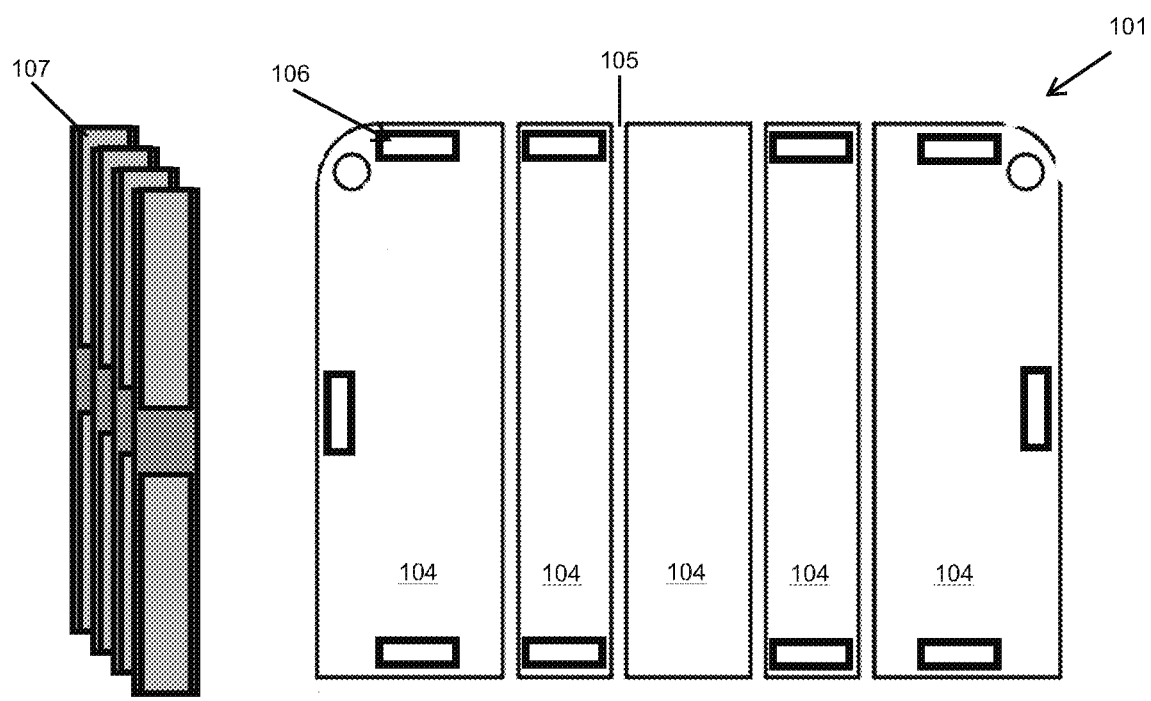
FIG. 57 is a front view of a fourth embodiment of an immobilization device of the present invention, the main body shown in a stowable configuration.
Figure 58:
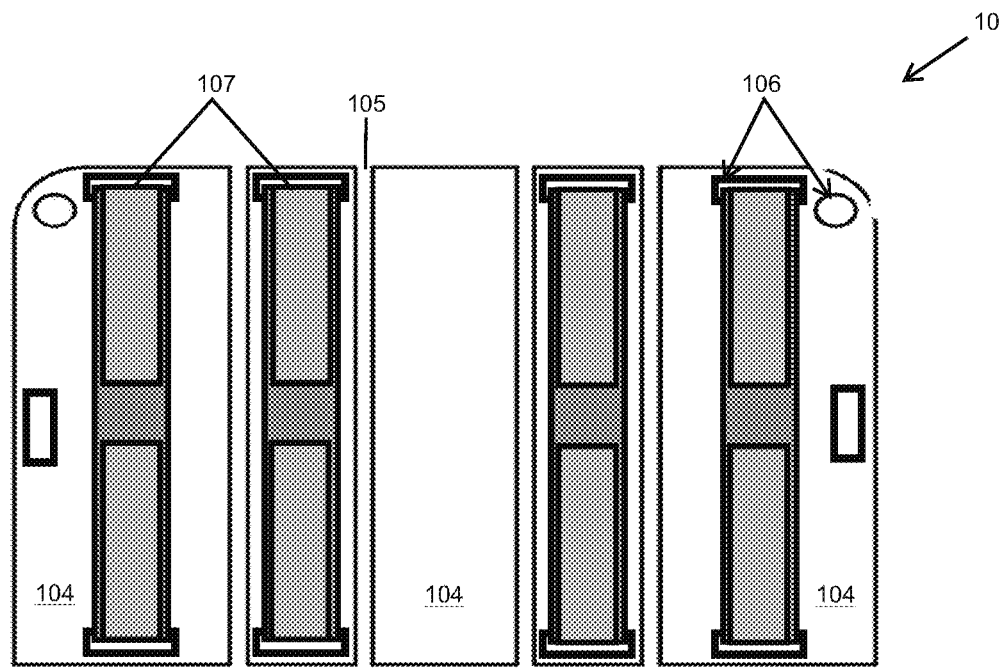
FIG. 58 is a front view of a fifth embodiment of an immobilization device of the present invention, the main body shown in a stowable configuration.
Figure 59:
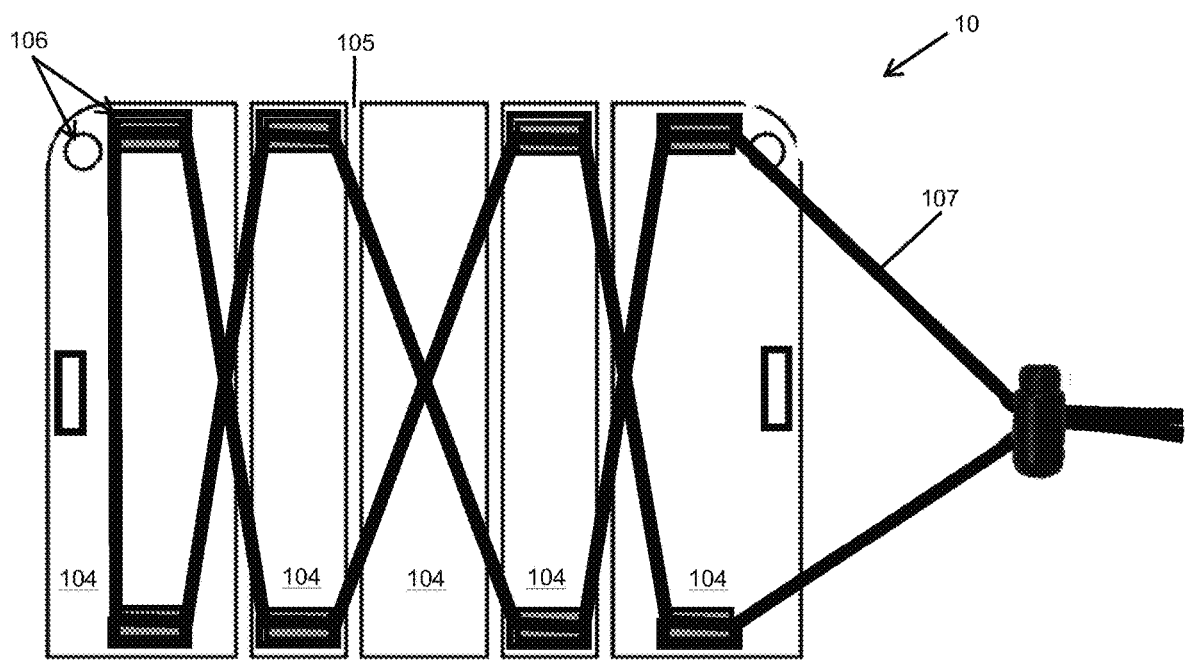
FIG. 59 is a front view of a sixth embodiment of an immobilization device of the present invention, the main body shown in a stowable configuration.

Referring to FIGS. 57, 58, and 59, in some embodiments, the main body is folded into a stowable configuration. Each panel is folded over adjacent panel(s) to minimize the surface area of the main body. In the stowable configuration, the panel connection angle is zero degrees. In other words, the panels fold on top of one another, accordion-style. In the stowable configuration, the segment connection angle is 180 degrees. In other words, the segments within each panel remain flat with respect to one another. Within each panel, the segments are not folded when the main body is in the stowable configuration.

Referring to FIGS. 15-35 and 43-56, in some embodiments, the main body is folded into various deployed configurations. In each deployed configuration, the panel connection angle is at or between 0 and 180 degrees. In each deployed configuration, the outermost segments of each panel are folded at an angle between 0 and 180 degrees. Thus, the segment connection angle is between 0 and 180 degrees. This folding at the segment connection angle within a panel provides strength and rigidity to the device in the lengthwise direction when the device is in the deployed configuration.

In some embodiments, the main body defines one or more hole 106, such as a segment hole. In some embodiments, at least one segment of each panel includes a segment hole 106. In some embodiments, the holes are sized and shaped such that the segment holes align with one another when the main body is folded into the stowable configuration. In some embodiments, the holes are sized and shaped to receive a fastener 107, such as a strap, band, cord, nail, or pin. The main body is maintained in the stowable configuration by threading the strap, band, cord, pin, or nail through the aligned holes. In some embodiments, the hole(s) 106 are elongated or slot-shaped. In some embodiments the strap, band, or cord is an elastic material. In some embodiments, the pin or nail is a rigid material, such as plastic or metal. In some embodiments, the strap is a zip tie or hook and loop fastener. In some embodiments, when the device is in the deployed configuration, the strap, band, cord, pin, or nail is threaded through the hole(s) to secure the device in the deployed configuration. In some embodiments, when the device is in the deployed configuration, the strap, band, cord, pin, or nail is threaded through the hole(s) to secure the device to the limb or extremity of a user or patient.

Figure 60:
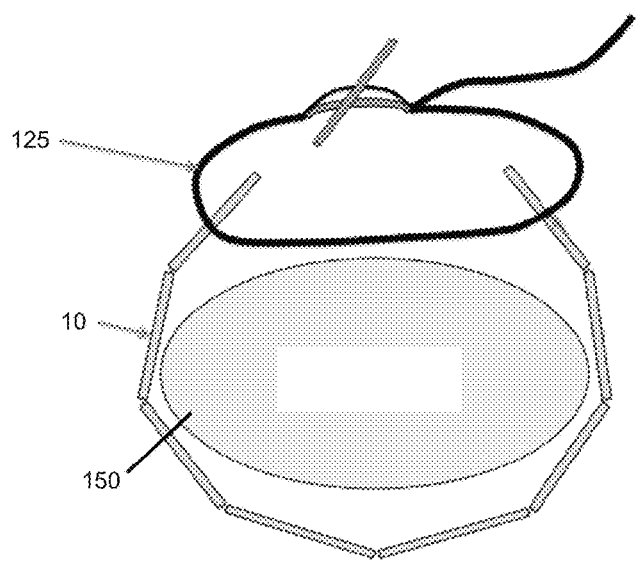
FIG. 60 is a cross-sectional view of a seventh embodiment of an immobilization device of the present invention, the main body shown in a deployed configuration used in connection with a tourniquet as a pelvic binder.

In some embodiments, the immobilization device is configured to be used with a tourniquet such that compressive loads are distributed across a larger area than is possible through the use of a tourniquet alone. Referring to FIG. 60, in some embodiments, when the device is in the deployed configuration, the strap, band, cord, pin, or nail is threaded through the hole(s) to secure the device body or trunk of the user, for example when used as a pelvic binder. In some embodiments, the present inventive concept is used in conjunction with a tourniquet such as described in U.S. Pat. Pub. No. US20150094756 as a pelvic binder. In some embodiments, the strap or band threaded through the holes (or slots) in the main body is a tourniquet such as described in U.S. Pat. Pub. No. US20150094756.

In some embodiments, the immobilization device in a deployed configuration is configured to restrain an appendage, limb, or extremity in a straight, 180 degree orientation. In some embodiments, the immobilization device in a deployed configuration is configured to restrain an appendage at an angle between 0 and 180 degrees, for example, 45 degrees or 90 degrees.

In some embodiments, the main body includes one or more pinch point 108. The pinch point is defined by opposed angle segments of adjacent segments of adjacent panels. The pinch point is configured to establish and maintain the panel connection angle at a predetermined angle when the opposed angle segments are folded over one another. In some embodiments, the pinch point includes one or more hole. The hole(s) are configured to receive a fastener. In this manner the opposed angle segments are fastened together when folded over one another. When the pinch point holes are aligned and a fastener is secured at the pinch point, the panels are secured in place establishing and maintaining the panel connection angle at the predetermined angle. In some embodiments, the fastener is a zip tie, nail, pin, brad, screw, or other fastener.

In some embodiments, the present inventive concept relates to methods for using an immobilization device. The method includes moving the immobilization device from the stowable configuration to the deployed configuration. In some embodiments, the method also includes moving the immobilization device to flat configuration. In some embodiments, the method also includes placing the immobilization device in the deployed configuration on the patient's (or user's) extremity to immobilize the user's extremity. In some embodiments, the method also includes securing the immobilization device in the deployed configuration to the user via the strap, cord, tourniquet or other fastener.

In some embodiments, the present inventive concept comprises a splint main body having a plurality of panels hingedly connected together, each panel having a plurality of segments hingedly connected together. In some embodiments, the main body is formed from a single piece of material defining a plurality of living hinges for defining and hingedly connecting the plurality of panels and segments. In some embodiments, the main body is formed from durable yet light-weight material, such as polypropylene, polyethylene, or any other light and durable material now known or later developed.

The splint is moveable between a stowable configuration and a flat configuration. In the stowable configuration, the various panels are folded over onto one another so as to minimize the overall surface area of the splint, thereby increasing portability and stowability of the splint. In some embodiments, a fastener, such as cords, cables, straps, and/or one or more other elongated member engages with one or more hole or slot of the splint, thereby retaining the splint in the stowed configuration. In some embodiments, the splint is included in a kit with one or more other medical device or supplies, such as gauze, gloves, or the like. In some embodiments, the one or more elongated member is formed from an elastic material, such as a bungee cord, elastic bands, or the like, thereby allowing the elongated member to selectively engage with and secure such other medical devices and/or supplies to and/or in relationship with the splint. In some embodiments, the splint and/or one or more elongated member includes a fastener to secure the splint to another object, such as to a belt, an article of clothing, a harness, a vehicle, or anywhere else it would be advantageous to have ready access to a splint or other medical supplies associated with the kit. In some embodiments, the fastener is a hook and loop fastener so that the splint and/or kit can be easily engaged with and/or disengaged from such other object.

In the flat configuration, each panel is parallel with, and extends from, each adjacent panel and each segment is parallel with, and extends from, each adjacent segment. From the flat configuration, the splint is selectively moveable to one of several deployed configurations. In a first deployed configuration the splint is configured to selectively restrain a person's arm or other appendage in a straight configuration such that the appendage is in an "open" (180) degree orientation. In a second deployed configuration the splint is configured to selectively restrain the appendage in an angled configuration. In some embodiments, the angle is 90 degrees. In other embodiments, the angle is between 180 and 90 degrees, such as 157 degrees (rotated 33 degrees away from the straight configuration), 135 degrees (rotated 45 degrees away from the straight configuration), or 123 degrees (rotated 67 degrees away from the straight configuration). In still other embodiments, the angle is less than 90 degrees.

In the first deployed configuration, each segment is rotated relative to an adjacent segment of the same panel while remaining generally parallel with each adjacent segment of adjacent panels. In this way, the splint gains rigidity for retaining each segment in general parallel relationship with each adjacent segment of adjacent panels. In the first deployed configuration, the splint is configured to wrap at least partially around a limb, such as an arm, and over a joint of the limb, such as the elbow, while the limb is in a straight configuration. In this way, the limb can be restrained in the straight configuration by securing the splint to the limb.

In the second deployed configuration, each segment is rotated relative to an adjacent segment of the same panel and at least some segments are rotated relative to an adjacent segment of an adjacent panel. In this way, the splint gains rigidity for retaining each segment in a general fixed relationship with each adjacent segment of adjacent panels. In the second deployed configuration, the splint is configured to wrap at least partially around a limb, such as an arm, and over a joint of the limb, such as the elbow, while the limb is in a bent configuration. In this way, the limb can be restrained in the bent configuration by securing the splint to the limb.

In some embodiments, the main body of the splint includes one or more pinch point for controlling the angle of the second deployed configuration. In some embodiments, the pinch point is created by forming opposed angled panels from opposed segments of one or more adjacent panel. In some embodiments, a first and second set of adjacent panels each includes respective opposed first and second outer segments and one or more respective inner segment extending therebetween. In some embodiments, each outer segment is divided into respective first 109 and second portions 110, with each first portion of each outer segment being hingedly coupled to each respective second portion while also being hingedly coupled to an adjacent first portion of an adjacent panel. In this way, the splint is moveable to the second deployed configuration by rotating respective first portions against each other, with the angle of the second deployed configuration being determined by the configuration of the first portions. In some embodiments, the first portions are configured to be secured together so as to secure the splint in the deployed configuration. In some embodiments, the first portions are configured to selectively rotate against and/or to be fastened to the second portion of at least one of the first and second panels, thereby providing greater strength and rigidity for retaining the angle of the second deployed configuration. In some embodiments, the main body of the splint includes a plurality of pinch points, thereby facilitating movement of the splint to a second deployed configurations, at one or more different angle.

In some embodiments, the main body of the splint defines one or more set of coordinating holes, such as circular holes, rectangular slots, or the like. In some embodiments, a first set of coordinating holes is configured such that a plurality of holes 106 through individual panels align when the splint is in the stowed configuration, creating a plurality of holes 106 through a plurality of panels so as to facilitate securing the splint in the stowed configuration. In some embodiments, a second set of coordinating holes is configured such that a plurality of holes 106 through individual segments can be utilized to engage with one or more strap, cord, or other elongated member for selectively securing the splint to a limb of a user.

In some embodiments, a third set of coordinating holes is configured such that a first hole 106 through a first portion of a first outer segment of a first panel is configured to align with a first hole 106 through a first portion of a first outer segment of a second panel, thereby enabling the respective first portions to be fastened together, such as with a bolt, a pin, a zip tie, or the like. In some embodiments, the second portion of the first outer segment of at least one of the first or second panels defines a second hole that is configured to align with the first holes when the first portions are folded against the respective second portion, thereby defining a stack-up hole through the stack-up of such portions so as to allow the first portions to be fastened to the respective second portion. In some embodiments, a third hole is defined by an adjacent inner segment such that a fastener, such as a zip tie, is able to extend from the third hole to the stack-up hole. In some embodiments, the fastener, such as a zip tie, extends through the stack-up hole and around an outer edge of the outer segment of the first or second panel.

In some embodiments, the splint is moveable from a flat configuration to a third deployed configuration. In the third deployed configuration, each panel is rotated relative to an adjacent panel and each segment is generally parallel with each adjacent segment of the same panel. In this way, the splint gains rigidity for retaining each segment in a general fixed relationship with each adjacent segment of the same panel. In the third deployed configuration, the splint is configured to wrap at least partially around a portion 150 of a person or animal, such as an abdomen or pelvis of such person or animal, thereby creating a barrier or support for the same. In some embodiments, the main body of the splint defines one or more slot 120 for receiving an elongated member 125, such as a tourniquet of U.S. Pat. No. 9,855,055, the entire disclosure of which is incorporated herein by reference. In this way, the splint is capable of distributing compressive loads across a larger area than is possible through the use of the elongated member alone.

In use, the splint is moved from a stowed configuration to a flat configuration by unfolding respective panels away from each other. From the flat configuration, the splint can be moved to a variety of deployed configurations to satisfy a variety of needs. In some circumstances, panel segments and/or segment portions are folded relative to each other so as to create longitudinal and/or angular rigidity. In some circumstances, panels are folded relative to each other so as to form lateral rigidity. One or more cable, strap, tourniquet, or other elongated member can be used with the splint to secure the splint to a user and/or for generating compressive loads for spreading across a portion of the splint.

In some embodiments, the splint is designed so that it can be connected to one or more other splint, such as through one or more sets of coordinating holes, thereby creating splints of various sizes and/or shapes. In this way, the combined splints can provide rigidity for a limb or other portion of a body having a length or girth too large for one splint alone. In some embodiments, pelvic binding can be achieved by attaching two or more splints together, such as in respective third configurations, so that they cover the circumference of a portion of the pelvic girdle of a user, such as ¾ of the pelvic girdle. In some embodiments, the width of a single splint is configured to provide sufficient stabilization to bind the pelvic girdle for pelvic splinting. In some embodiments, the width of a single splint is seven (7) inches. In some embodiments, the splint is fabricated from a material that is form fitting and/or the splint is configured to otherwise create a snug, comfortable fit.

While the present general inventive concept has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.

It is also to be understood that the following claims are intended to cover all of the generic and specific features of the invention herein described, and all statements of the scope of the invention which, as a matter of language, might be said to fall there between. Hence, the proper scope of the present general inventive concept should be determined only by the broadest interpretation of the appended claims so as to encompass all such modifications as well as all relationships equivalent to those illustrated in the drawings and described in the specification.

Finally, it will be appreciated that the purpose of the annexed Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

What is claimed is:

1. An extremities immobilization device comprising:
   an elongated main body comprising a plurality of panels with a hinged panel connection between a first of said plurality of panels and an adjacent panel; and
   each of said plurality of panels further comprising a plurality of segments with a hinged segment connection between a first of said plurality of segments and an adjacent segment;
   wherein a panel connection angle is defined by a geometric angle between said first panel and said adjacent panel; and
   wherein a segment connection angle is defined by a geometric angle between said first segment and said adjacent segment.

2. The immobilization device of claim 1, wherein when said main body is folded into a deployed configuration, said panel connection angle is at or between 0 and 180 degrees.

3. The immobilization device of claim 2, further comprising one or more pinch point comprising opposed angle segments of adjacent segments of adjacent panels, wherein said pinch point is configured to establish and maintain said panel connection angle at a predetermined angle when said opposed angle segments are folded over one another.

4. The immobilization device of claim 3, wherein said opposed angle segments further comprise one or more holes configured to receive a fastener, thereby allowing the angle segments to be fastened together when said opposed angle segments are folded over one another.

5. The immobilization device of claim 2, wherein the segment connection angle is 180 degrees.

6. The immobilization device of claim 1, wherein at least one segment of each panel comprises a segment hole, wherein said segment holes align with one another when said main body is folded into said stowable configuration.

7. The immobilization device of claim 1, wherein when said main body is folded into a stowable configuration, said first panel is folded over the adjacent panel to minimize surface area of the main body and said panel connection angle is zero degrees.

8. The immobilization device of claim 7, wherein the segment connection angle is 180 degrees.

9. The immobilization device of claim 1, wherein when said main body is unfolded into a flat configuration, said first panel is unfolded and flat with respect to the adjacent panel and said panel connection angle is 180 degrees.

10. The immobilization device of claim 9, wherein the segment connection angle is 180 degrees.

11. The immobilization device of claim 1, wherein said hinged panel connection is a living hinge.

12. The immobilization device of claim 1, wherein said hinged segment connection is a living hinge.

13. The immobilization device of claim 1, wherein said main body is formed of a single piece of material and each of said hinged panel connection and said hinged segment connection is a living hinge.

14. A system for immobilizing extremities comprising:
    a tourniquet attached to the immobilization device of claim 1.

15. A method for using an extremities immobilization device, the method comprising:
- moving an immobilization device from a stowable configuration to a deployed configuration, wherein the immobilization device comprises an elongated main body comprising a plurality of panels with a hinged panel connection between a first of said plurality of panels and an adjacent panel and each of said plurality of panels further comprising a plurality of segments with a hinged segment connection between a first of said plurality of segments and an adjacent segment;
- wherein a panel connection angle is defined by a geometric angle between said first panel and said adjacent panel; and
- wherein a segment connection angle is defined by a geometric angle between said first segment and said adjacent segment.

16. The method of claim 15, wherein when said main body is folded into said stowable configuration, said first panel is folded over the adjacent panel to minimize surface area of the main body and said panel connection angle is zero degrees and when said main body is folded into said deployed configuration, said panel connection angle is at or between 0 and 180 degrees.

17. The method of claim 15, wherein when said main body is folded into said stowable configuration, said segment connection angle is 180 degrees and when said main body is folded into said deployed configuration, said panel connection angle is less than 180 degrees.

18. The method of claim 15, wherein said step of moving an immobilization device from said stowable configuration to said deployed configuration comprises:
- moving said immobilization device from said stowable configuration to a flat configuration; and
- moving said immobilization device from said flat configuration to said deployed configuration;
- wherein when said main body is unfolded into said flat configuration, said first panel is unfolded and flat with respect to the adjacent panel and said panel connection angle is 180 degrees.

19. The method of claim 15, further comprising:
- placing said immobilization device in said deployed configuration on a user's extremity to immobilize the user's extremity.

* * * * *